(12) United States Patent
Isogawa et al.

(10) Patent No.: US 6,300,135 B1
(45) Date of Patent: *Oct. 9, 2001

(54) BLOOD COMPONENT DEPOSITION-PREVENTING AGENT, METHODS USING THEM, AND BLOOD TEST WARE AND MATRIXES

(75) Inventors: Hironobu Isogawa; Hideo Anraku, both of Shinnanyou (JP)

(73) Assignee: Sekisui Kagaku Kogyo Kabushiki Kaisha, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/204,065

(22) Filed: Dec. 3, 1998

Related U.S. Application Data

(62) Division of application No. 08/648,132, filed as application No. PCT/JP95/00461 on Mar. 17, 1995, now Pat. No. 5,888,824.

(30) Foreign Application Priority Data

Sep. 19, 1994 (JP) .................................................. 6-223093

(51) Int. Cl.⁷ .................................................... G01N 33/48
(52) U.S. Cl. ............................ 436/18; 436/36; 252/408.1
(58) Field of Search ........................... 252/408.1; 436/18, 436/63, 69, 68

(56) References Cited

U.S. PATENT DOCUMENTS

| | | | |
|---|---|---|---|
| 3,839,200 | * 10/1974 | Gigou et al. | 210/22 |
| 4,053,696 | * 10/1977 | Herrle et al. | 526/65 |
| 4,069,185 | 1/1978 | Sullivan . | |
| 4,239,664 | 12/1980 | Teng et al. . | |
| 4,276,172 | 6/1981 | Henne et al. | 210/490 |
| 5,418,235 | * 5/1995 | Mueller et al. | 514/252 |

FOREIGN PATENT DOCUMENTS

| | | |
|---|---|---|
| 32 07 270 A1 | 1/1983 | (DE) . |
| 42 39 499 A1 | 5/1994 | (DE) . |
| 0 454 593 A1 | 6/1993 | (EP) . |
| 0 545 209 A1 | 6/1993 | (EP) . |
| 0 353 710 A2 | 5/1994 | (EP) . |
| 2 555 074 | 5/1985 | (FR) . |

* cited by examiner

*Primary Examiner*—Lyle A. Alexander
(74) *Attorney, Agent, or Firm*—Connolly Bove Lodge & Hutz

(57) ABSTRACT

This invention has for its object to provide a blood component deposition-preventing agent and a blood coagulation accelerator, which are substantially indifferent to blood coagulation activity and serum chemistry parameters and a plastic blood test ware and a blood test matrix which do not confound measured values. The invention relates to a blood component deposition-preventing agent comprising a random copolymer of a monomer component (a) giving a water-soluble homopolymer and a monomer component (b) giving a water-insoluble homopolymer, a blood coagulation accelerator comprising a substantially blood-insoluble antimicrobial composition comprising a carrier and, as supported thereon, an antimicrobial metal, and a blood test ware or matrix carrying them on its inside wall or surface.

26 Claims, No Drawings

BLOOD COMPONENT DEPOSITION-PREVENTING AGENT, METHODS USING THEM, AND BLOOD TEST WARE AND MATRIXES

This application is a divisional of Ser. No. 08/648,132 filed Jul. 5, 1996, now U.S. Pat. No. 5,888,824 which is the national filing of PCT/JP/95/00461, filed Mar. 17, 1995.

TECHNICAL FIELD

The present invention relates to a blood component deposition-preventing agent and a blood coagulation accelerator for use in the laboratory examination of a blood sample, particularly in hematology, serum biochemistry, and immunoserology, methods using them, and blood examination ware and matrixes.

BACKGROUND TECHNOLOGY

With recent advances in testing techniques, the chemical, immunoserological and hematological examinations of blood have witnessed a remarkable mechanization so that it is by now certain that only if properly prepared samples were provided, such examinations could be carried through in short periods of time. For example, even in the outpatient setting, the doctor would be able to make a diagnosis based on blood examination data, thus contributing much to the diagnosis and therapy of diseases, As to the pretreatment for hematological examinations using whole blood as a sample, mere admixing of the blood with an anticoagulant, which is not time-consuming, is sufficient so that the sample can be almost immediately set in an analyzer.

However, in biochemical or immunoserological examinations using the serum fraction of blood, it is necessary to coagulate the blood once and, then, separate the serum by centrifugation or the like and the procedure is rather time-consuming. Therefore, in order to reduce the time required for the whole examination procedure from the pretreatment of a sample to the output of tent data, mere shortening of the analysis time by mechanization of the analytical procedure is insufficient and it is necessary to shorten the time required for separation of serum.

Meanwhile, glassware has heretofore been used as the blood examination vessel for accommodating the blood to be test, allowing it to coagulate therein, and separating the serum by centrifugation. However, glassware is vulnerable to mechanical impact and, when it is broken the test sample that issues out or splashes may cause the examiner to be infected by pathogenic bacteria and, as an additional problem, the necessary blood sampling for examination adds to a burden on the patient. For these reasons, plastic vessels have come into popular use in recent years. However, such plastic ware has been found disadvantageous in that the formed elements of the blood (hereinafter referred to as blood components) such as platelets, various blood proteins, and especially the fibrins which are formed in the final stage of the blood coagulation process, are very liable to deposit on the inside wall of the plastic ware and thereby exert untoward effects on examination results. Moreover, as will be described in detail hereinafter, it is common practice to employ a mineral substance or an organic substance such as ellagic acid, as a blood coagulation accelerator in blood examination ware but such blood coaglation accelerator tends to encourage deposition of said blood components on the vessel wall and the blood components once deposited will not easily be detached from the inside wall of the vessel under the routine conditions of centrifugation such as about 1000 to 1800 G.times.5 minutes. As a result owing to the high shear force of centrifugation acting on the interface between the inside wall and the clot the platelets and red blood cells are destroyed and their contents leak out to affect the examination results.

To overcome these disadvantages, Japanese Kokai Publication Sho-58-105063 and Japanese Kokai Publication Sho-58-105064 proposed a method which comprises disposing a blood coagulation accelerator and a nonionic subfactant concomitantly on the inside wall of the ware, for instance. However, with the recent rapid development of high sensitivity techniques in the field of immunoserological examination, analogues of nonionic surfactants are being used as sensitizers on more and more occasions. If the test serum is contaminated with a nonionic surfactant, oversensitizing reactions occur in immunoserologic parameters to present the problem of inaccuracy leading to false positive tests.

On the other hand, for efficient separation of plasma from the blood to be analyzed, there is a protocol involving addition of a blood anticoagulant such an ethylenediamineteraacetic acid salt or a citrate to the blood sample. In hematological examinations using an anticoagulant, too, the deposition of blood components, particuarly platelets, on the plastic surface may be a cause of trouble, although the frequency of the trouble is not high. If platelets stick to the inside wall of blood test ware, the platelet count may show on abnormally low value or confound blood coagulation function values. Moreover, where an emergency chemical examination is required, it is common practice to use a heparin salt which is a kind of anticoagulant but if the deposition of platelets occurs in such cases, various enzymes of platelet origin leak out into the plasma with time so that the related examination parameters tend to show abnormally high values. These events are less frequent as compared with the coagulation of blood and have so far attracted little attention but are now pointed out as a serious problem as an omnibus, accurate and rapid blood examination is demanded.

The above problem of deposition of blood components has been pointed out with reference to plastic blood test ware but recently the adverse influences of the deposition and activation of platelets on examination results have been pointed out for blood examination glassware as well and improvements are being sought just as for plastic ware.

Since plastic ware for blood examination is intrinsically low in the potential to activate blood coagulation XII factor and XI factor, it takes by far a longer time for the blood to coagulate in plastic ware than in glassware and, therefore, plastic ware has so far been of low practical value.

Therefore, attempts have been made to shorten the blood coagulation time by coating the inside wall of blood test ware with a finely divided mineral substance such as glass, kaolin, bentonite, silica, cerite, or the like or a blood coagulation accelerator such an ellagic acid as taught in Japanese Kokai Publication Sho-58-195151 or accommodating in the ware a substantially blood-insoluble and chemically inert nonwoven cloth or plastic sheet matrix on Which said finely divided particles have been imobilized as taught in Japanese Kokal Publication Sho-58-105064.

When a blood coagulation-accelerating substance is to be coated on the inside wall of a blood test ware or immobilized on a carrier, a suspension of finely divided particles of such substance either in pure water or in a mixture of alcohol and pure water is prepared and spray-coated on the inner surface of the ware or a carrier material is dipped in such a suspension, dried, cut to size, and accommodated within the blood test ware.

However, such a treating suspension is susceptible to the attack of microorganisms and unless it is properly handled, may cause contamination of a blood sample with microorganisms. Furthermore, when a water-soluble macromolecular compound such as polyvinylpyrrolidone or a modified cellulose is incorporated in said suspension as a binder for said coagulation accelerator powder or a viscosity adjusting agent for the suspension as is generally practiced, the water-soluble macromolecular compound serves as a good nutrient source for microorganisms so that the above-mentioned tendency of the treating suspension to be a microbial contamination risk factor in further encouraged.

As the proliferation of microorganisms progresses, condensation products will be accumulated in the treating suspension to cause troubles such a clogging of the spray nozzle, marked loan of coated surface evenness, and biases in the density of particles immobilized on the carrier in the dipping stage, all of which add up to measurement errors. The risk of microbial contamination is not confined to the current risk associated with degradation of the treating suspension but is a persistent drawback for the shelf-life of the ware unless the method for storage of the ware is wholesome.

Therefore, unless manufactured in a sterile environment, a blood test ware containing a blood coagulation accelerator may have to be sterilized with actinic radiation such as gamma-rays, electron beams, etc. or a chemically reactive gas such as ethylene oxide gas. In any of such procedures the radiation dose or the concentration of the reactive gas, heating temperature, exposure time and other sterilizing conditions must be adjusted according to the contamination status prior to sterilization and, thus, very delicate control is required.

Moreover, where the sterilizing load has been severely contaminated, rugged sterilizing conditions are required so that the load may sustain irreversible modification, deformation, and other damages. Moreover, in the storage after sterilization, the sterility once established will be jeopardized unless the ware is properly packaged.

One of the possible effective approaches to solving the above problems is to impart antimicrobial activity to the very coagulation accelerator. By such a technique, the above-mentioned microbial contamination would be inhibited and even if sterilization be needed, mild sterilizing conditions would be sufficient, with the result that the physical and chemical changes of the load due to sterilization could be prevented or suppressed. Furthermore, the packaging of the blood test ware could be simplified.

As regards antibacterial and antifungal agents which are generally used for prevention of microbial contamination, a large number of compounds inclusive of those for food use are already known and in use. However, the large majority of these antibacterial and antifungal agents are water-soluble and, therefore, if the blood is drawn into a blood test ware in which a blood anticoagulant supplemented with such an antimicrobial agent has been accommodated, the antimicrobial agent may dissolve out into the blood to confound various chemical tests. Moreover, when the antibacterial or antifungal agent is a water-soluble heavy metal salt, it modifies the enzymes associated with blood coagulation and the resulting deactivation of the enzymes prevent coagulation of the blood and make it difficult to achieve the objective such as separation of serum.

Where the specimen to be analyzed is plasma, it is a routine procedure to mix the blood with an anticoagulant and centrifuge the mixture to separate plasma from the solid fraction. Generally speaking, in order to avoid contamination of plasma with substances liberated from formed elements of the blood and other matter and the consequent interference with tests, the plasma obtained by centrifuging blood in the above manner is transferred to a different container and stored. Recently, however, for the purpose of protecting the examiner against infection via the patient's blood, a procedure which does not require a transfer to another ware is demanded. Therefore, the use of a plasma separator comprising a thixotropic fluid as disclosed in Japanese Kokai Publication Hei-2-168159 or the use of a separator for provision of a partition between the plasma layer and the solid component layer as taught in Japanese Kokai Publication Hei-5-26873 has been recently employed.

However, the inside surface of the plastic ware is hydrophobic and the blood cells and proteins are adsorbed thereon as mentioned above. Particularly platelets are adsorbed with a high affinity and because LDD (lactic dehydrogenase), CPK (creatine kinase), K (potassium), etc. occur at higher levels in platelets than in plasma, these components are released from the platelets adsorbed on the plastic surface and it is inevitable that the values of these test parameters are considerably affected.

Therefore, even if the above-mentioned procedure of providing a partition between the plasma layer and the solid component layer is followed, the gradual release of enzymes and others from the blood cells adsorbed on the inside wall of the ware containing the plasma is unavoidable and interferes with tests. These adverse effects are particularly remarkable when the plasma is stored in the refrigerator for reexamination.

Having overcome the above disadvantages of the prior art, the present invention has for its primary object to provide a blood component deposition-preventing agent which is capable of inhibiting deposition of blood components effectively without causing the problem of false positive reactions in the immunoserological tests.

The second object of the present invention is to provide a blood coagulation accelerator comprising an antibacterial composition which has its own blood coagulation-accelerating activity and yet substantially does not interfere with blood coagulation activity or confound serum biochemical tests.

The third object of the present invention is to provide a plastic ware and a matrix for blood examination which do not influence test values owing to release of substances from blood cells even when used in tests on plasma.

DISCLOSURE OF INVENTION

The essential feature of the first aspect of the present invention is that a random copolymer comprising 10 to 90 mol % of a monomer component (a) the homopolymer of which is water-soluble and 90 to 10 mol % of a monomer component (b) the homopolymer of which in water-insoluble is used as a blood component deposition-preventing agent.

The essential feature of the second aspect of the present invention is that a blood coagulation accelerator is provided by supporting an antimicrobial metal on a carrier material and incorporating the resulting substantially blood-insoluble antimicrobial composition.

The essential feature of additional aspect of the present invention which is composed of first and second aspects resides in methods using said blood component deposition-preventing agent and said blood coagulation accelerator and in the blood test ware and matrix.

The first and second aspects of the present invention are now described in detail.

The blood component deposition-preventing agent according to the first aspect of the present invention comprises a random copolymer. The monomer component(a) as a constituent of said random copolymer is not limited in kind only if its homopolymer is water-soluble,thus including vinylpyrrolidone, vinyl alcohol, ethylene oxide, salts of acrylic acid, salts of styrenesulfonic acid, salts of vinyl phosphonic acid, allylamine salts, hydroxymethyl(meth) acrylate, glycosylethyl(meth)acrylate, saccharides such as glucose, amino acids such as glutamic acid, and so on. These monomers can be used singly or in combination.

The monomer component (b) as the other constituent of said random copolymer is not limited in kind, either, only if its homopolymer is water-insoluble, thus including ethylene, propylene, propylene oxide, vinyl acetate, vinyl chloride, alkyl(meth)acrylates, styrene, acrylonitrile, acrolein, and so on. These monomers can be used singly or in combination.

The random copolymer comprising said monomer component (a) and monomer component (b) can be provided by the known addition polymerization, polycondensation, or other technique.

However, from the standpoint of availability, it is advantageous to prepare the random copolymer using vinylpyrrolidone or vinyl alcohol as monomer component (a) and vinyl acetate as monomer component (b). As commercial products, Luviskol VA grade numbers VA73, VA64, VA55, VA37, and VA28 are available from BASF as typical vinylpyrrolidone-vinyl acetate random copolymers and Unitika Poval grade numbers E-180, UMR-10M, UMR-30L, and UMR-150L are available from Unitika Ltd. as typical vinyl alcohol-vinyl acetate random copolymers.

In the above random copolymer, the proportion of monomer component (a) the homopolymer of which is water-soluble is within the range of 10 to 90 mol % and that of monomer component (b) the homopolymer of which is water-insoluble is within the range of 90 to 10 mol %.

If the proportion of monomer component (a) the homopolymer of which is water-soluble exceeds 90 mol %, the resulting random copolymer will not be much different in characteristics from the homopolymer of monomer component (a) so that the rate of adsorption on the inside wall of blood test ware and on the matrix surface is decreased and the solubility in blood is too high. As a consequence, when blood is drawn into the blood teat ware, the random copolymer is washed out from the inner surface of the ware and the matrix surface so that it cannot play the role of preventing deposition of blood components.

On the other hand, if the proportion of monomer component (a) the homopolymer of which is water-soluble is less than 10 mol %, the copolymer will not be much different in characteristics from the homopolymer of monomer component (b) and become substantially insoluble in blood so that it may not play the role of preventing deposition of blood components. When a combination of this blood component deposition-preventing agent and a blood coagulation accelerator or a blood anticoagulant is applied to the inside wall of the blood test ware or the matrix surface and dried, a blood-insoluble film is formed on the surface of the blood coagulation accelerator or anticoagulant so that blood coagulation factors XII, XI, etc. cannot bind to the surface of the blood coagulation accelerator, with the result that the coagulation of blood is not hastened and the reduced solubility of the blood anticoagulant leads to an insufficient anticoagulant effect.

For the above reasons, the random copolymer for use in the present invention should be such that said monomer component (a) whose homopolymer is water-soluble and said monomer component (b) whose homopolymer is water-insoluble account for 10 to 90 mol % and 90 to 10 mol %, respectively.

The blood test ware of the present invention comprises a vessel and, as disposed on its inner surface, the blood component deposition-preventing agent according to the first aspect of the present invention.

In this construction, the amount of the blood component deposition-preventing agent present on the inner surface of the vessel is preferably in the range of $1 \times 10^{-10}$ to $1 \times 10^{-2}$ g/cm$^2$. If the amount of the blood component deposition-preventing agent is less than $1 \times 10^{-10}$ g/cm$^2$, the deposition-preventing effect will not be sufficient, while the presence of more than $1 \times 10^{-2}$ g/cm$^2$ of the deposition-preventing agent will be liable to affect various test values.

The material for the vessel of the blood test ware of the invention can be any of thermoplastic resint thermosetting resin, modified natural resin, and glass. The thermoplastic resin mentioned above includes but is not limited to polyethylene, polypropylene poly(4-methylpentene-1), polystyrene, poly(methyl methacrylate), poly(vinyl chloride), poly(ethylene terephthalate), poly(butylene terephthalate), poly(styrene-co-acrylonitrile), poly(styrene-co-maleic anhydride), poly(styrene-co-acrylic acid), poly (styrene-co-methyl methacrylate), poly(ethylene-co-propylene), poly(ethylene-co-acrylic acid), poly(ethylene-co-acrylic ester), poly(vinyl acetal), and poly(vinyl butyral). The thermosetting resin mentioned above includes but is riot limited to unsaturated polyester resin, epoxy resin, and epoxy-acrylate resin. The modified natural resin includes but is not limited to cellulose acetate, cellulose propionate, cellulose acetate butyrate, ethylcellulose, and ethylchitin.

The blood test ware of the present invention can be manufactured by causing the blood component deposition-preventing agent of the invention to be present on the inner wall of a blood test vessel or tube by a variety of alternative methods. Thus, for example, the method which comprises kneading the blood component deposition-preventing agent of the invention into a plastic batch for the molding of a vessel and molding the kneaded mixture by the injection molding, blow molding or other technique and the method which comprises dissolving the blood component deposition-preventing agent in pure water or alcohol, applying the solution to the inside wall of the vessel by spray coating or dip coating, and drying the coat can be mentioned.

In addition to the presence of the blood component deposition-preventing agent comprising the random copolymer according to the present invention, the blood test ware of the present invention may have a serum/plasma separator comprising a thixotropic fluid or a separator material functioning as a partition between the serum or plasma layer and the blood solid component layer.

The serum/plasma separator includes a composition comprising liquid acrylic resin, chlorinated polybutene or liquid dicyclopentadiene (DCPD) as a matrix and a finely divided inorganic powder such as microfine silica, alumina or glass particles as an auxiliary component for specific gravity adjustment and thixotropy.

By allowing such a partition-forming agent to be present, the storage life of serum or plasma can be increased without confounding test values.

The blood component deposition-preventing matrix of the present invention comprises a support and, as disposed on its surface, a blood component deposition-preventing agent comprising the random copolymer according to the first aspect of the present invention. The blood component deposition-preventing matrix is put to use as accommodated in a blood test tube or vessel. The support of said blood component deposition-preventing matrix can be any of the known supports. The shape of the support is not limited and may, for example, be pellets, a sheet, a nonwoven fabric, or a woven fabric. The possible raw material of the support includes thermoplastic resin, thermosetting resin, and modified natural resin, among others. The thermoplastic resin mentioned just above includes but is not limited to polyethylene, polypropylene, poly(4-methylpentene-1), polystyrene, poly(methyl methacrylate), poly(vinyl chloride), poly(ethylene terephthalate), poly(butylene terephthalate), poly(styrene-co-acrylonitrile), poly(styrene-co-maleic anhydride), poly(styrene-co-acrylic acid), poly(styrene-co-methyl methacrylate), poly(ethylene-co-propylene), poly(ethylene-co-acrylic acid), poly(ethylene-co-acrylic enter), poly(vinyl acetal), and poly(vinyl butyral). The thermosetting resin includes unsaturated polyester resin, epoxy resin, and epoxy-acrylate resin.

The amount of said blood component deposition-preventing agent comprising the random copolymer on the surface of said blood component deposition-preventing support is preferably in the range of $1\times10^{-10}$ to $1\times10^{2}$ g/cm$^2$. If the amount of the blood component deposition-preventing agent is less than $1\times10^{-10}$ g/cm$^2$, the deposition-preventing effect will not be sufficient, while the presence of more than $1\times10^{-2}$ g/cm$^2$ of the deposition-preventing agent will be liable to affect various test values.

The blood component deposition-preventing matrix of the present invention can be manufactured by causing the blood component deposition-preventing agent of the invention to be present on the surface of a support by a variety of alternative methods. Thus, for example, the method which comprises kneading the blood component deposition-preventing agent of the invention into a plastic batch for the fabrication of the support and molding the kneaded mixture by the injection molding, blow molding or other technique and the method which comprises dissolving the blood component deposition-preventing agent in pure water or alcohol, applying the solution to the surface of the support by spray coating or dip coating, and drying the coat can be mentioned.

While the blood component deposition-preventing agent of the present invention can be used independently as described a above, it can be used in combination with an adsorbent inorganic material, e.g. mineral substances such as glass, kaolin, bentonite, silica, cerite, etc., or in combination with an organic blood coagulation-accelerating substance such as ellagic acid. It can also be used in combination with an anticoagulant such as an ethylenediaminetetraacetic acid salt, citric acid salt, heparin salt, oxalic acid salt, or the like or an antiglycolytic agent such as fluorides, mannose, and so on.

When poly(vinylpyrrolidone-co-vinyl acetate) is selected as the blood component deposition-preventing agent of the invention and used in combination with said adsorbent inorganic material comprising at least one member of the group consisting of glass, kaolin, bentonite, silica and cerite, the vinylpyrrolidone content of said poly(vinylpyrrolidone-co-vinyl acetate) is preferably in the range of 10 to 70 mol %. If the proportion of vinylpyrrolidone is less than 10 mol %, the agent will be stuck to the inside wall of the vessel so that no clot-exfoliating effect can be obtained. If the proportion of vinylpyrrolidone exceeds 70 mol %, the agent will dissolve into the blood and not remain on the inner surface of the vessel so that no clot-exfoliating effect can be obtained.

The adsorbent inorganic material mentioned above is preferably a material not containing particles larger than 50 μm and having a mean particle diameter of not more than 30 μm. Particularly for shortening the clotting time, the adsorbent inorganic substance is preferably silica and a porous silica containing not less than 20 weight % of an amorphous fraction is particularly preferred. Such an adsorbent inorganic substance promotes activation of blood coagulation factors on contact with blood and, also, accelerates aggregation of platelets.

In such cases, the amount of poly(vinylpyrrolidone-co-vinyl acetate) to be present on the inside wall of the blood test vessel is preferably in the range of $1\times10^{-10}$ to $1\times10^{-2}$ g/cm$^2$. On the other hand, the amount of the adsorbent inorganic substance to be present on the inside wall of the blood test vessel is preferably in the range of $1\times10^{-6}$ to $1\times10^{-2}$ g/cm$^2$. If it in less than $1\times10^{-2}$ g/cm$^2$, no blood coagulation-accelerating effect will be obtained. If the limit of $1\times10^{-2}$ g/cm$^2$ is exceeded, chances for inaccurate tests will be increased. The combined amount of said two materials is preferably not greater than $1\times10^{-2}$ g/cm$^2$.

With the blood test ware carrying the poly(vinylpyrrolidone-co-vinyl acetate) and adsorbent inorganic substance in combination, the blood coagulation factors are rapidly activated so that the clotting time is considerably shortened and, at the same time, the adhesion of the resulting clot to the inside wall of the blood test vessel is successfully prevented. As consequences, release of the serum from the clot is assisted, contamination of the serum with components of the clot is eliminated, and the serum yield is remarkably increased.

In order that said adsorbent inorganic substance may effectively exhibit its blood coagulation-accelerating action, each of the linseed oil absorption value, BET specific surface area value, and resistivity value is preferably within a certain range.

The linseed oil absorption value and BET specific surface area value represent the magnitude of surface area of the adsorbent inorganic substance and the surface area value is also related with the degree of surface porosity of the adsorbent inorganic substance. Therefore, the degree of surface porosity can be known from the oil absorption and specific surface area values. The preferred adsorbent inorganic substance for use in the present invention preferably has a linseed oil absorption value of 20 to 40 ml/100 g and a BET specific surface area value of 5000 to 30000 cm$^2$/g.

The linseed oil absorption value is the value measured in accordance with Japanese Industrial Standards (JIS) K-5101. The BET specific surface area value means the value found by determining the amount of gas which completely covers the surface as a monomolecular layer from the amount of gas adsorbed on the surface of an adsorbent inorganic substance, the prevailing equilibrium pressure, and the saturation vapor pressure of adsorbed gas and multiplying the result by the mean sectional area of adsorbed gas molecules. As the adsorption gas, nitrogen gas, oxygen gas, argon gas, methane gas, etc. can be selectively employed. By this procedure, the Surface area inclusive of fine pores which cannot be measured by the linseed oil absorption method can be determined. In the coagulation of blood, factor XII, that is to say the contact factor, is activated but for this activation it is necessary that the three substances of factor XII, prekalikrein and macromolecular kininogen must form a complex and be adsorbed on the surface of a foreign matter and it is said that the adsorption in the deficiency in one or two of the three does not result in the activation.

In this connection, when an adsorbent inorganic substance used for the purpose of accelerating blood coagulation is a substance having a vary large surface area, the free factor XII, prekalikrein and macroolecular kininogen not forming a complex are adsorbed in an increased proportion on its surface, that is to say the proportion of the tripartite complex necessary for the activation of factor XII is decreased so that the blood coagulation-accelerating effect is rather sacrificed. Conversely when the surface area of the adsorbent inorganic substance is too small, the probability of adsorption of coagulation factors is decreased so that the desired blood coagulation-accelerating effect cannot be expected.

Therefore, the preferred adsorbent inorganic substance has a linseed oil absorption value of 20 to 40 ml/100 g and a BET specific surface area value of 5000 to 30000 $cm^2/g$.

The preferred resistivity value of the adsorbent inorganic substance is not larger than $1\times10^{10}$ $\Omega\cdot cm$ and, for still better results, not larger than $5\times10^4$ $\Omega\cdot cm$. The resistivity value is the reciprocal of the electrical conductivity value and represents the value at atmospheric temperature. It is supposed that the above resistivity of the adsorbent inorganic substance contributes to a sustained alignment of electric potential distribution between the protein and the adsorbent inorganic substance and prevention of change in the conformation of the protein.

When poly(vinylpyrrolidone-co-vinyl acetate) as said blood component deposition-preventing agent and a salt of ethylenediaminetetraacetic acid, a salt of citric acid, a heparin salt, a salt of oxalic acid, or the like as said blood anticoagulant are used in combination, the vinyl acetate content of said poly(vinylpyrrolidone-co-vinyl acetate) is preferably in the range of 30 to 90 mol %.

The ethylenediaminetetraacetate mentioned above can be any of those salts which are conventionally employed, such as disodium ethylenediaminetetraacetate, dipotassium ethylenediaminetetraacetate, tripotassium ethylenediaminetetraacetate, and so on.

The salt of citric acid can also be the salt conventionally used as a blood anticoagulant and may for example be trisodium citrate.

The heparin salt mentioned above may also be a salt conventionally used as an Anticoagulant such as heparin sodium, heparin lithium, etc.

The salt of oxalic acid mentioned above can also be any salt that is conventionally used as an anticoagulant, thus including sodium oxalate, potassium oxalate, etc.

Any of the same known techniques as described hereinbefore can be used for causing said blood coagulation accelerator, blood anticoagulant, and antiglycolytic agent to be present on the inside wall of a blood test vessel or on the surface of a matrix to be accommodated in the blood test vessel. An exemplary procedure comprises causing the blood component deposition-preventing agent of the invention to be present on the inside wall of a blood test vessel or the surface of a support in the first place and, then, applying the blood coagulation accelerator, blood anticoagulant and/or antiglycolytic agent to the inside wall or surface by way of spray-coating or dipping. An alternative procedure comprises dissolving or suspending all the components in a suitable medium, applying the solution or suspension to the substrate surface by way of spray-coating or dipping, and drying the coat.

Since the blood component deposition-preventing agent of the present invention is a random copolymer comprising 10 to 90 mol % of a monomer component (a) which would give a water-soluble homopolymer and 90 to 10 mol % of a monomer component (b) which would give a water-insoluble homopolymer, it is structurally distinct from the known block copolymer of a hydrophilic monomer component such as a nonionic surfactant with a hydrophobic monomer component or the known graft polymer corresponding to such a block copolymer. While the nonionic surfactant mentioned above is coming into popular use as a useful sensitizer in immunoserological tests, the blood component deposition-preventing agent of the present invention is substantially free from the action of a sensitizer and, as such, does not induce test errors such as false positive reactions.

In the second aspect of the present invention, a blood coagulation accelerator is provided by supporting an antimicrobial metal on a support or carrier and the resulting antimicrobial composition which is substantially insoluble in blood is employed.

The support mentioned above must be eliminated from the serum at centrifugation after the coagulation of blood for separation of serum. Since the specific gravity of human serum is 1.02 to 1.03, the above support should have a specific gravity of not less than 1.03 and preferably not less than 1.05.

The support material is not critical in kind only if the above requirement in regard to specific gravity is satisfied, thus including a variety of inorganic materials such as zeolite, montmorillonite, ceramics, glass, insoluble phosphates, etc. and a variety of organic materials such as graphite and ion exchange resins. Particularly preferred are silicic acid compounds or silica series substances such as zeolite, montmorillonite, ceramics, etc. and insoluble phosphates, all of which per se have blood coagulation-accelerating properties as well.

The antimicrobial metal for use in the present invention is not particularly limited, thus including the corresponding salts and organometal compounds whose metal elements are copper and silver which belong to the Ib group of the periodic table of the elements, zinc, cadmium and mercury in the lib group, germanium, tin and lead in the IVa group, lanthanids such as cerium and so on. In view of the balance between toxicity and utility, silver, copper, zinc, and cerium are preferred.

The antimicrobial composition contained in the blood coagulation accelerator according to the second aspect of the present invention comprises said support and, as supported thereby, said bacteriostatic metal. The mode of supporting of said bacteriostatic metal on the support includes ion exchange, complex formation, and inclusion (as a clathlate). Other supporting modes are not satisfactory because of the risk of release of the metal into the blood.

The antimicrobial composition mentioned above is preferably in the form of a finely divided powder with a large surface area and the preferred particle size is 0.01 to 500 $\mu m$. If the particle diameter is less than 0.01 $\mu m$, a higher bacteriostatic action can be expected but in the centrifugation step following completion of blood coagulation for separation of serum, the composition may remain in serum under the routine centrifugal conditions of about 1000 to 1800 G×5 minutes to cause clouding of the serum and other troubles such that the supported metal and the metal inherently contained in the serum are assayed together to introduce a positive error to the test value.

On the other hand, If the particle diameter exceeds 500 μm, the antimicrobial composition tends to be dispersed unevenly in the preparation of a suspension of the blood coagulation accelerator, with the result that the expression of antimicrobial activity is localized near the surface of the antimicrobial composition ao that no bacteriostatic/fungistatic effect can be expected. Particularly preferred is an antimicrobial composition having a mean particle diameter of 0.01 to 50 μm.

The minimum dose of said antimicrobial composition, like that of antisepatic and antifungal agents in general, can be chosen according to MBC (minimal bactericidal concentration) and MFC (mininmal fungicidal concentration). However, it is preferable to insure that the concentration of the antimicrobial agent in a suspension of the blood coagulation accelerator of the invention in purified water, for instance, will be not less than 0.1 μg/ml.

As to the maximum dose of said antimicrobial composition, objectionable events such as hemolysis would be encountered if a large amount of insoluble matter finds its way into the blood. Therefore, it is preferable to determine the formulation so that the concentration in blood in the event of release into the blood will not exceed 0.5 g/ml.

The above-mentioned blood coagulation accelerator can be prepared by mixing the above antimicrobial composition with a mineral blood coagulation-accelerating agent such as glass, kaolin, bentonite, silica, cerite, etc. or an organic blood coagulation-accelerating substance such as ellagic acid.

The above blood coagulation accelerator can be suspended in pure water or physiological saline to prepare a suspension and this suspension be contacted with the sample blood to shorten the clotting time.

Furthermore, the above blood coagulation accelerator can be used to construct a blood test ware having high blood coagulation-accelerating activity by suspending the accelerator in pure water or alcohol/purified water and spraying the inside wall of the blood test vessel with the suspension or immersing a support such as a nonwoven fabric or a plastic sheet in said suspension and, after drying and cutting the support to size, accommodating the cutting in the blood test vessel.

The above-mentioned blood coagulation-accelerating suspension may contain a water-soluble macromolecular compound such as polyvinylpyrrolidone or modified cellulose as a binder for the coagulation accelerator or a viscosity control agent for the suspension.

The antimicrobial composition comprising silver, copper, zinc or the like as immobilized on zeolite, montmorillonite, ceramic, insoluble phosphate or the like, which is contained in the blood coagulation accelerator of the present invention destroys microorganisms invading the purified water or alcohol/purified water in which the accelerator has been suspended and is capable of preventing microbial contamination during storage of the blood test ware manufactured using the accelerator and, yet, will no dissolve into the blood so that the function of the blood coagulation accelerator is not adversely affected, nor does it interfere with blood examination values. Moreover, because the antimicrobial composition itself has blood coagulation-accelerating activity, the specific activity of the whole blood coagulation accelerator as a complex artifact is not compromised. The reason why sufficient antimicrobial efficacy can be expected despite the fact that the antimicrobial metal contained in the antimicrobial composition of the invention is little released in the form of free ions is probably that active oxygen is generated in the vicinity of the supported metal.

The essential feature of the third aspect of the present invention resides in the following constructions of (3-1), (3-2), (3-3), (3-4), and (3-5).

(3-1)

A blood test ware characterized in that $1\times10^{-10}$ to $1\times10^{-2}$ g/cm$^2$ of a polyvinylpyrrolidone having a weight average molecular weight of 100000 to 2000000 is disposed on the inside wall of a plastic vessel and, in addition, at least one blood anticoagulant selected from the group consisting of the salts of ethylenediaminetetraacetic acid, heparin, citric acid, and oxalic acid in disposed in said plastic vessel.

(3-2)

A blood test ware characterized in that a composition comprising the following components (1), (2), and (3) is disposed on the inside wall thereof, and a blood test matrix characterized in that a composition comprising the following components (1), (2), and (3) is disposed on the surface thereof, and which is substantially insoluble in blood and physicochemically substantially inert to blood and has a specific gravity of not less than 1.03 and a maximum projected length of not less than 1 mm.

(1) a polyvinylpyrrolidone having a weight average molecular weight of 100000 to 2000000

(2) a blood anticoagulant (3) a finely divided powder which is substantially insoluble in blood and physicochemically substantially inert to blood and has a specific gravity of not less than 1.08 and a particle diameter of 1 mμ to 100 μ

(3-3)

A blood test ware characterized in that a composition comprising the following components (1), (2), and (3) is disposed on the inside wall thereof, and a blood test matrix characterized in that a composition comprising the following components (1), (2), and (3) is disposed on the surface thereof, and which is substantially insoluble in blood and physicochemically substantially inert to blood and has a specific gravity of not less than 1.03 and a maximum projected length of not less than 1 mm.

(1) a random copolymer comprising 10 to 90 mol % of a monomer component (a) the homopolymer of which is water-soluble and 90 to 10 mol % of a monomer component (b) the homopolymer of which is water-insoluble (2) a blood anticoagulant (3) a finely divided powder which is substantially insoluble in blood and physicochemically substantially inert to blood and has a specific gravity of not less than 1.08 and a particle diameter of 1 mμ to 100 μ

(3-4)

A blood test ware characterized in that a composition comprising the following components (1), (2), and (3) is disposed on the inside wall thereof, and a blood test matrix characterized in that a composition comprising the following components (1), (2), and (3) is disposed on the surface thereof, and which is substantially insoluble in blood and physicochemically substantially inert to blood and has a specific gravity of not less than 1.03 and a maximum projected length of not less than 1 mm.

(1) a nonionic surfactant (2) a blood anticoagulant (3) a finely divided powder which is substantially insoluble in blood and physicochemically substantially inert to blood and has a specific gravity of not less than 1.08 and a particle diameter of 1 mμ to 100 μ

(3-5)

A blood test ware characterized in that a composition comprising the following components (1), (2), (3), and (4) is disposed on the inside wall thereof, and a blood test matrix characterized in that a composition comprising the following components (1),(2), (3), and (4) is disposed on the surface thereof, and which is substantially insoluble in blood and physicochemically substantially inert to blood and has a specific gravity of not less than 1.03 and a maximum projected length of not less than 1 mm.
  (1) at least one blood component deposition-preventing agent selected from the group consisting of silicone oil, polar group-containing modified silicone oil, polyhydric alcohol partial esters, polyhydric alcohol complete esters, and poly(propylene oxide)
  (2) a water-soluble macromolecular compound
  (3) a blood anticoagulant
  (4) a finely divided powder which is substantially insoluble in blood and physicochemically substantially inert to blood and has. a specific gravity of not less than 1.08 and a particle diameter of 1 m$\mu$ to 100 $\mu$ The third aspect of the present invention is now described in detail.

The blood test ware (3-1) comprises a plastic vessel and, as disposed on the inside wall thereof, $1\times10^{-10}$ to $1\times10^{-2}$ g/cm$^2$ of a polyvinylpyrroidone having a weight average molecular weight of 100000 to 2000000. If the amount of said polyvinylpyrrolidone Is less than $1\times10^{-10}$ g/cm$^2$, it will be impossible to obtain the desired blood component deposition-preventing effect, while more than $1\times10^{-2}$ g/cm$^2$ of polyvinylpyrrolidone will interfere with blood examinations.

The weight average molecular weight of polyvinylpyrrolidone can be determined by the conventional methods such as ultracentrifugation or the light scattering method. As an alternative, the viscosity average molecular weight (Mv) is first calculated from the viscosity value known as K value by means of the following equation (1) and the weight average molecular weight (Mw) is then calculated by means of the following equation (2) [V. Buehler, U. Klodwig. Acta Pharm., Techn., 30. No, 4 (1984)].

$$Mv=22.22\times(K+0.075\times K^2)^{1.65} \quad (1)$$

$$Mw\approx Mv \quad (2)$$

The weight average molecular weight of said polyvinylpyrrolidone is 100000 to 2000000. If it is less than 100000, the polyvinylpyrrolidone will dissolve into blood and disappears from the inside wall of the blood test ware so that the blood component deposition-preventing effect cannot be obtained, if the molecular weight exceeds 2000000, spray or other coating workability is sacrificed. Therefore, the above range is essential. The preferred range is 300000 to 1500000 and. the still more preferred range is 600000 to 1500000.

Further disposed in this blood test ware is at least one blood anticoagulant selected from the group consisting of the salts of ethylenediamninetetraacetic acid, heparin, citric acid, and oxalic acid, and fluorides.

The above-mentioned salt of ethylenediaminetetraacetic acid can be any of the salts which are Conventionally used as blood anticoagulants, such as disodium ethylenediaminetetraacetate, dipotassium ethylenediaminetetraacetate, and tripotassiumn ethylenediaminetetraacetate, among others.

The above-mentioned salt of citric acid can also be any of the salts conventionally used as blood anticoagulants, such as trisodium citrate, among others.

The heparin salt mentioned above can be a salt of heparin which is commonly used as a blood anticoagulant, thus including heparin sodium, heparin lithium and so on.

The above-mentioned salt of oxalic acid can be any of those oxalates which are conventionally used as blood anticoagulants, thus including sodium oxalate and potassium oxalate, among others.

Among the fluorides mentioned above are sodium fluoride and potassium fluoride which are conventionally used as antiglycolytic agents.

In the above blood test ware may be further accommodated a material capable of establishing a partition between a plasma layer and a solid component layer, such as a plasma separator comprising a thixotropic fluid or a separating member. The plasma separator may for example be a composition comprising chlorinated polybutene or dicyclopentadiene (DCPD) resin as a main component and a finely divided inorganic powder such as powdered silica, alumina or glass as a viscosity control and thixotropic agent. When such a partitioning material is provided, the blood test were can store the plasma for a long time without adverse effects on test data.

The method of using the blood test ware comprises drawing the blood sample into the ware and after thorough mixing of the anticoagulant and the blood, centrifuging the ware to separate the plasma.

Since a specified quantity of a specified grade of polyvinylpyrrolidone is present on the inside wall of the vessel in the above blood test ware, corpuscular elements and proteins in the blood are prevented from adhering to the inside wall surface. Moreover, since the blood anticoagulant is accommodated in the vessel, coagulation of the blood is prevented. Furthermore, in the embodiment where a partition-forming substance is provided within the vessel, the plasma can be stored in stable condition for a long time without influences on test values.

The blood test ware (3-2) comprises a vessel and, as disposed on the inside wall of said vessel, a composition comprising the following components (1), (2) and (3), and the corresponding blood test matrix comprises a support and, as disposed on its surface, a composition comprising the following components (1), (2) and (3), and is substantially insoluble in blood and physicochemically substantially inert to blood and has a specific gravity of not less than 1.03 and a maximum projected length of not less than 1 mm.
  (1) a polyvinylpyrrolidone having a weight average molecular weight of 100000 to 2000000
  (2) a blood anticoagulant
  (3) a finely divided powder which is substantially insoluble in blood and physicochemically substantially inert to blood and has a specific gravity of not less than 1.08 and a particle size within the range of 1 m$\mu$ to 100 $\mu$ The description for (3-1) applies to said polyvinylpyrrolidone having a weight average molecular weight of 100000 to 2000000 (1).

The description for (3-1) applies to said blood anticoagulant (2).

The finely divided powder (3) is now described. using a medium which is a good solvent for both the polyvinylpyrrolidone and blood anticoagulant, a homogeneous solution can be prepared. However, when the inside wall of a plastic vessel is coated with such a solution by spray-coating or dip-coating and the coated vessel is allowed to stand in the upright position, the solution Is not retained on the inside wall but flows down to the bottom of the vessel. In that event, the solution forms a thick dry film on the bottom to seriously interfere with redissolution of the anticoagulant in the blood so that the blood undergoes local coagulation and in the subsequent step of accommodating a plasma separator most of the anticoagulant is buried under the plasma separator and fails to contact the blood introduced so that the expected effect is not accomplished. The finely divided powder (3) has the property to considerably improve the retention of the dispersion on the plastic vessel by suppressing the sagging tendency so that the above problem is neatly solved.

The above effect of the finely divided powder (3) is probably attributed to the following. Thus, as the finely divided powder is adsorbed on the inside wall surface, a large number of fine projections and recesses are formed on the inside wall to increase the surface area and the retentivity of the solution is increased as the result of surface tension.

If the specific gravity of said finely divided powder (3) is less than 1.08, the powder (3) could remain in the plasma even after centrifugal separation of the blood to interfere with blood tests. Therefore, the specific gravity is restricted to 1.08 or more.

If the particle diameter of finely divided powder (3) is less than 1 m$\mu$ the fine particles tend to form a dense film upon concentration to dryness to interfere with redissolution of the blood anticoagulant. On the other hand, if 100 $\mu$ is exceeded, the separation and sedimentation rate of particles in a mixed dispersion of polyvinylpyrrolidone and blood anticoagulant is increased to sacrifice the retentivity on the inside wall surface of the vessel. Therefore, the particle diameter should be limited to the above range. The preferred range is 1 to 50 $\mu$.

The level of addition of finely divided powder (3) is not particularly critical but a sufficient effect can be obtained when it is present in a proportion of 5 weight % or less.

The material of said finely divided powder (3) is not so critical and can be any of such materials as, for example, poly(meth)acrylic acid esters, poly(vinyl chloride), fluororesins, polyamides, polyesters, polyoxyalkylenes, polyurethane, urea resin, melamine resin, epoxy resin, phenolic resin, cellulose, chitin, modified cellulose, modified chitin, and their copolymers and crosslinked polymers. Even polystyrene, polyethylene and polypropylene which cannot be used alone on account of their low specific gravities can be utilized when a conventional inorganic filler such as silica, talc or the like has been kneaded into them for specific gravity adjustment. These powders can be manufactured in the conventional manner, for example by suspension polymerization or pulverization and size selection. In the above blood test ware may be disposed a material capable of providing a partitioning wall between the plasma layer and the solid component layer, such as a plasma separator comprising a thixotropic fluid or a separatory member.

The blood test matrix according to (3-2) carries a composition comprising the above-mentioned components (1), (2) and (3) on its surface and provides for the same effect as the blood test ware described above. The blood test matrix should not affect the blood examination and, therefore, is designed to be substantially insoluble in blood and physicochemically substantially inert to blood. This blood test matrix has a specific gravity of not less than 1.03 and a maximum projected length. of not less than 1 mm. If the specific gravity is less than 1.03, the matrix floats without sinking in the blood sample to interfere with the examination. If the maximum projected length is less than 1 mm, workability is sacrificed.

The above blood test matrix is used as accommodated in the blood test vessel. The known support materials can be used for the fibrication of said blood test matrix. There is no particular limitation on matrix configuration, and pellets, sheet, nonwoven cloth, woven cloth, etc. can be mentioned as examples. The raw material is not particularly restricted, either, and a variety of materials similar to those mentioned for said component (3) can be utilized.

The blood test ware according to (3-3) comprises a vessel and, as disposed on its inside wall surface, a composition comprising the following components (1), (2) and (3). The corresponding blood test matrix comprises a support and, as disposed on its surface, a composition comprising the following components (1), (2) and (3), and is substantially insoluble in blood and physicochemically inert to blood and has a specific gravity of not less than 1.03 and a maximum projected length of not less than 1 mm.

(1) a random copolymer comprising 10 to 90 mol % of a monomer components (a) which would give a water-soluble homopolymer and 90 to 10 mol % of a monomer component (b) which would give a water-insoluble homopolymer.

(2) a blood anticoagulant (3) a finely divided powder which is substantially insoluble in blood and physicochemically substantially inert to blood and has a specific gravity of not less than 1.08 and a particle diameter in the range of 1 m$\mu$ to 100 $\mu$ The above-mentioned random copolymer (1) comprises a monomer component (a) which would give a water-soluble homopolymer and a monomer component (b) which would give a water-insoluble homopolymer. The monomer component (a) which would give a water-soluble homopolymer that can be used includes but is not limited to vinylpyrrolidone, vinyl alcohol, ethylene oxide, salts of acrylic acid, salts of styrenesulfonic acid, salts of vinylphosphonic acid, s allylamine salts, hydroxymethyl (meth) acrylate, glycosylethyl (meth)acrylate, saccharides such as glucose, and amino acids such as glutamic acid. These monomers can be Used alone or as a mixture.

The monomer component (b) which would give a water-insoluble homopolymer that can be used includes but is not limited to ethylene, propylene, propyleneoxide, vinyl acetate, vinyl chloride, alkyl (meth)acrylates, styrene, acrylonitrile, and acrolein. These monomers can be used alone or as a mixture.

The random copolymer comprising said monomer components (a) and (b) can be produced typically by the known addition polymerization reaction or polycondensation reaction. In view of the availability of materials, it is advantageous to synthesize the random copolymer by using vinylpyrrolidone or vinyl alcohol as the monomer component (a) and vinyl acetate as the monomer component (b). As commercial products, Luviskol VA grade numbers VA73, VA64, VA55, VA37, and VA28 are available from BASF as typical vinylpyrrolidone-vinyl acetate random copolymers and Unitika Poval grade numbers n-180, UMR-10M, UMR-30L, and UMR-150L are available from Unitika Ltd. as typical vinyl alcohol-vinyl acetate random copolymers.

In the above random copolymer, the proportion of monomer component (a) the homopolymer of which is water-soluble is within the range of 10 to 90 mol % and that of monomer component (b) the homopolymer of which is water-insoluble is within the range of 90 to 10 mol %.

If the proportion of monomer component (a) the homopolymer of which is water-soluble exceeds 90 mol %, the resulting random copolymer will not be much different in characteristics from the homopolymer of monomer component (a) so that the rate of adsorption on the inside wall of the blood test ware and on the matrix surface is decreased and the solubility in blood is too high. As a consequence, when blood is drawn into the blood test ware, the random copolymer is washed out from the inside wall of the ware or the matrix surface so that it cannot play the role of preventing deposition of blood components.

On the other hand, if the proportion of monomer component (a) whose homopolymer is water-soluble is less than 10 mol %, the copolymer will not be much different in characteristics from the homopolymer of monomer component (b) and be substantially insoluble in blood so that it may not play the role of preventing deposition of blood components. When a combination of. this blood component deposition-preventing agent with a blood coagulation accelerator or a blood anticoagulant is applied to the inside wall of a blood test vessel or the matrix surface and dried, a blood-insoluble film is formed on the surface of the blood coagulation accelerator or blood anticoagulant so that blood coagulation factors XII, XI, etc. cannot bind to the surface of the blood coagulation accelerator, with the result that the coagulation of blood is not hastened and the reduced solubility of the blood anticoagulant leads to an insufficient anticoagulant effect.

For the above reasons, the random copolymer for use in the present invention should be such that said monomer component (a) whose homopolymer is water-soluble and said monomer component (b) whose homopolymer is water-insoluble account for 10 to 90 mol % and 90 to 10 mol % respectively.

The amount of said random copolymer is preferably $1 \times 10^{-10}$ to $1 \times 10^{-2}$ g/cm$^2$. If it is less than $1 \times 10^{-10}$ g/cm$^2$, deposition of corpuscular components and proteins will not be sufficiently precluded. If the amount of the random copolymer exceeds $1 \times 10^{-2}$ g/cm$^2$, various test parameter values will be confounded.

The above blood test ware according to (3-4) comprises a vessel and, as disposed on its inside wall, a composition comprising the following components (1), (2) and (3) and the corresponding blood test matrix comprises a support and, as disposed on its surface, a composition of the following components (1), (2) and (3) and is substantially insoluble in blood and physicochemically substantially inert to blood and has a specific gravity of not less than 1.03 and a maximum projected length of not less than 1 mm.

(1) a nonionic surfactant (2) a blood anticoagulant (3) a finely divided powder which is substantially insoluble in blood and physiochemically substantially inert to blood and has a specific gravity of not less than 1.08 and a particle diameter in the range of 1 m$\mu$ to 100 $\mu$ The above nonionic surfactant (1) that can be used includes but is not limited to ethylene glycol/propylene glycol series, alkyllalkylene oxide series, and alkylene oxide/silicone series block copolymers and graft copolymers, inclusive of the corresponding modified polymers. Particularly preferred are surfactants with HLB (hydrophilic-lypophilic balance) numbers not less than 10.

The preferred proportion of said nonionic surfactant (1) is $1 \times 10^{-10}$ to $1 \times 10^{-2}$ g/cm$^2$. If it is less than $1 \times 10^{-10}$ g/cm$^2$, deposition of corpuscular components and proteins will not be sufficiently precluded. If the amount of the surfactant exceeds $1 \times 10^{-2}$ g/cm$^2$, various test parameter values could be confounded.

The blood test ware according to (3-5) comprises a vessel and, as disposed on the inside wall surface thereof, a composition comprising the following components (1), (2), (3) and (4), and the corresponding blood test matrix comprises a support and, as disposed on its surface, a composition comprising the following components (1), (2), (3) and (4) and is substantially insoluble in blood and physiochemically substantially inert to blood and has a specific gravity of not less than 1.03 and a maximum projected length of not less than 1 mm.

(1) At least one blood component deposition-preventing agent selected from the group consisting of silicone oil, modified silicone oil containing polar groups, partial esters of polyhydric alcohols, complete esters of polyhydric alcohols, and poly(propylene oxide)

(2) a water-soluble macromolecular substance (3) a blood anticoagulant (4) a finely divided powder which is substantially insoluble in blood and physicochemically substantially inert to blood and has a specific gravity of not less than 1.08 and a particle diameter In the range of 1 m$\mu$ to 100 $\mu$ The silicone oil (1) that can be used includes but is not limited to dimethylpolysiloxane, methylhydrogenpolysiloxane, and methylphenylpolyslloxane. The polar group-modified silicone oil (1) includes oils obtainable by introducing polar groups such as hydroxyl, amino, carboxyl, epoxy, etc. into dimethylpolysiloxane, methylhydrogenpolysiloxane, methylphenylpolysiloxane and other silicone oils.

The above-mentioned partial or complete esters of polyhydric alcohols (1) are compounds available on introduction of fatty acid molecules to some or all of the alcoholic hydroxyl functions of the respective polyols such as glycerol, sorbitol, polyphenol, etc.

The blood component deposition-preventing agent (1) includes, in addition to the substances mentioned above, poly(propylene oxide) and other substances.

The preferred amount of said blood component deposition-preventing agent (1) is $1 \times 10^{-10}$ to $1 \times 10^{-2}$ g/cm$^2$. If the amount of (1) is less than $1 \times 10^{-10}$ g/cm$^2$, no sufficient deposition-preventing effect on corpuscular elements and proteins will be obtained. If it exceeds $1 \times 10^{-2}$ g/cm$^2$, various test parameter values will be interfered with.

The water-soluble macromolecular compound (2) that can be used includes but is not limited to poly(ethylene oxide), poly(vinyl alcohol), polyvinylpyrrolidone, poly(sodium acrylate), polyethyleneimine, sodium alginate, starch, pullulan, methylcellulose, hydroxyethylcellulose, hydroxypropylcellulose, carboxymethylcellulose, cellulose acetate phthalate, gum arabic, guns tragacanth, locust bean gum, guar gum, pectin, carrageenan, phaseleran, tamarind seed polysaccharide, glue, gelatin and casein. Particularly preferred are polyvinylpyrrolidone, poly(ethylene oxide) and poly(vinyl alcohol).

The water-soluble macromolecular compound (2) serves to prevent the water-insoluble matter from covering the blood anticoagulant to inhibit its solubility in blood.

The preferred amount of said water-soluble macromolecular compound (2) is $1 \times 10^{-10}$ to $1 \times 10^{-2}$ g/cm$^2$. If it is less than $1 \times 10^{-10}$ g/cm$^2$, no sufficient deposition-preventing effect on corpuscular elements and proteins will be obtained.

If the amount of the compound exceeds $1 \times 10^{-2}$ g/cm$^2$, various test parameter values could be confounded.

EXAMPLES

The following examples are intended to describe the present invention In further detail and should by no means be construed as defining the scope of the invention.

Examples 1-1 to 1-27

The present invention is now described with reference to the examples using the 9 kinds of random copolymers listed in Table 1-1.

TABLE 1-1

| Copolymer structure | Manufacturer | Trade name | Grade designation | Mol % of monomer (b) |
|---|---|---|---|---|
| Vinylpyrrolidone-vinyl acetate random copolymer | BASF | Luviskol VA | VA73 | 35 |
| | | | VA64 | 46 |
| | | | VA55 | 56 |
| | | | VA37 | 75 |
| | | | VA28 | 84 |
| Vinyl alcohol-vinyl acetate random copolymer | UNITIKA | Unitika Poval | E-180 | 10 |
| | | | UMR-10M | 35 |
| | | | UMR-30L | 60 |
| | | | UMR-150L | 80 |

For use as the blood component deposition-preventing agent, aqueous solutions of the vinylpyrrolidone-vinyl acetate random copolymers shown in Table 1-2 (only the grade numbers are shown in Table 1-2) in pure water were prepared to the concentrations (weight %) specified in Table 1-2. Moreover, aqueous solutions of the vinyl alcohol-vinyl acetate random copolymers shown in Table1-3 (only the grade numbers are given in Table 1-3) in pure water were prepared to the concentrations (weight %) specified in Table 1-3. However, UMR-150L only was dissolved in methanol.

About 50 μl of each solution was sprayed into a poly (ethylene terephthalate) blood sampling tube of 10 ml capacity according to Table 1-2 or Table 1-3 and dried in an air-current dryer at 60° C. to provide a blood test ware. Fresh rabbit blood, 3 ml, was taken in each blood test ware and allowed to stand at the room temperature of 23 to 25° C. After complete coagulation of blood was confirmed at 4 hours, the adhesion of the clot to the inside wall of the blood test ware was visually evaluated. As a result, none of the tubes showed adhesion of the clot. Then, the tubes were centrifuged at 1300 G (25° C.) for 5 minutes and the adhesion of the clot on the inside wall of the blood test ware was visually evaluated again. At the same time, the yield of serum that separated out was determined. As a result, none of the tubes showed adhesion of the clot to the inside wall. The serum yields are shown in Table 1-2 and Table 1-3.

TABLE 1-2

| | Copolymer | | Serum yield after |
|---|---|---|---|
| Example | Grade | Concentration (%) | centrifugation (ml) |
| 1-1 | VA73 | 0.05 | 1.4 |
| 1-2 | VA73 | 1.00 | 1.4 |
| 1-3 | VA73 | 5.00 | 1.5 |
| 1-4 | VA64 | 0.05 | 1.4 |
| 1-5 | VA64 | 1.00 | 1.5 |
| 1-6 | VA64 | 5.00 | 1.5 |
| 1-7 | VA55 | 0.05 | 1.5 |
| 1-8 | VA55 | 1.00 | 1.5 |
| 1-9 | VA55 | 5.00 | 1.4 |
| 1-10 | VA37 | 0.05 | 1.5 |
| 1-11 | VA37 | 1.00 | 1.4 |
| 1-12 | VA37 | 5.00 | 1.4 |
| 1-13 | VA28 | 0.05 | 1.4 |
| 1-14 | VA28 | 1.00 | 1.4 |
| 1-15 | VA28 | 5.00 | 1.4 |

TABLE 1-3

| | Copolymer | | Serum yield after |
|---|---|---|---|
| Example | Grade | Concentration (%) | centrifugation (ml) |
| 1-16 | E-180 | 0.05 | 1.4 |
| 1-17 | E-180 | 1.00 | 1.4 |
| 1-18 | E-180 | 5.00 | 1.5 |
| 1-19 | UMR-10M | 0.05 | 1.4 |
| 1-20 | UMR-10M | 1.00 | 1.5 |
| 1-21 | UMR-10M | 5.00 | 1.4 |
| 1-22 | UMR-30L | 0.05 | 1.5 |
| 1-23 | UMR-30L | 1.00 | 1.5 |
| 1-24 | UMR-30L | 5.00 | 1.4 |
| 1-25 | UMR-150L | 0.05 | 1.4 |
| 1-26 | UMR-150L | 1.00 | 1.5 |
| 1-27 | UMR-150L | 5.00 | 1.4 |

Comparative Example 1-1

As the blood component deposition-preventing agent, a 0.05 weight % aqueous solution of vinylpyrrolidone homopolymer (manufactured by BASF, Luviskol K-30TM, weight average molecular weight 30000) was used in lieu of a 0.05 weight % solution of vinylpyrrolidone-vinyl acetate random copolymer. The test was carried out in otherwise the same manner as in Example 1-1. Four hours after blood sampling, complete coagulation of blood was confirmed and the adhesion of the clot to the inside wall of the blood teat ware was visually evaluated. As a result, clot deposits were found. In the evaluation of clot deposits on the inside wall of the ware after centrifugation, not only clot deposits were found but also marked hemolysis was observed. The serum yield after centrifugation was 1.4 ml.

Comparative Example 1-2

As the blood component deposition-preventing agent, a 0.05 weight % aqueous solution of vinyl alcohol homopolymer (manufactured by Unitika Ltd., Unitika Poval (tradename) UF200G) was used in lieu of a 0.05 weight % solution of vinylpyrrolidone-vinyl acetate random copolymer. The test was carried out in otherwise the same manner as in Example 1-1. Four hours after blood sampling, complete coagulation of blood was confirmed and the adhesion of the clot to the inside wall of the blood test ware was visually evaluated. As a result, clot deposits were found. In the evaluation of clot deposits on the inside wall of the ware after centrifugation, not only clot adhesion spots but also moderate hemolysis was observed. The serum yield after centrifugation was 1.4 ml.

Comparative Example 1-3

As the blood component deposition-preventing agent, a 0.05 weight % methanolic solution of vinyl acetate-ethylene copolymer (manufactured by Hoechst Gosei.Co.; mobinil (tradename) E45) was used in lieu of a 0.05 weight % solution of vinylpyrrolidone-vinyl acetate random copolymer. The test was carried out in otherwise the same manner as in Example 1-1. Four hours after blood sampling, complete coagulation of blood was confirmed and the degree of adhesion of the clot to the inside wall of the blood test ware was visually evaluated. AS a result, marked adhesion was found. In the examination of clot adhesion to the inside wall of the ware after centrifugation, marked adhesion was found. The serum yield after centrifugation was 0.0 ml.

Comparative Example 1-4

The test procedure of Example 1-1 was repeated except that the ware carrying no blood component deposition-preventing agent (that is an untreated poly(ethylene terephthalate) tube of 10 ml capacity) was used as the blood test ware, Four hours after blood sampling, complete coagulation of blood was confirmed and the degree of adhesion of the clot to the inside wall of the blood test ware was visually evaluated. As a result, marked deposits were found. In the examination of clot adhesion to the inside wall of the ware after centrifugation, not only marked deposits of the clot but also hemolysis was observed. The serum yield after centrifugation was not more than 0.5 ml.

The results of Examples 1-1 to 1-27 and Comparative Examples 1-1 to 1-4 indicate that whereas the poly(ethylene terephthalate) blood sampling tube (Comparative Example 1-4) inherently has the property to strongly bind blood components, the blood component deposition-preventing agent random copolymer of the present invention exhibits an excellent deposition-preventing effect. The serum yields in Examples 1-1 to 1-27 were approximately 50% of the whole blood, indicating that substantially the whole amount of serum was recovered. Comparative Examples 1-1 and 1-2 correspond to the case where, of the monomer composition of the random copolymer for use in the present invention, the proportion of the monomer component which would yield a water-insoluble homopolymer is 0 mol %, and Comparative Example 1-3 correspond to the case in which the proportion of the same monomer component is 100 mol %. comparative Examples 1-1 and 1-2 were obviously inferior giving punctuate blood clot deposits on the inside wall, although the serum yield was not so affected, and, in addition, showed hemolysis. In Comparative Example 1-3, marked clot deposits were found and the recovery of serum was infeasible. All of the cases are deviating from the requirement of the invention that the proportion of the monomer compound giving a water-insoluble homopolymer should be 10 to 90 mol %, thus failing to inhibit deposition of blood components.

Example 2-1

Using a vinylpyrrolidone-vinyl acetate random copolymer (manufactured by BASF, Luviskol (tradename) VA73, vinyl acetate content ca 36 mol %) as the blood component deposition-preventing agent and a finely divided silica powder (mean particle diameter 4.0 μm, the linseed oil absorption determined in accordance to JIS K 5101=30 ml/100 g, BET specific surface area 12000 cm²/g, resistivity as the reciprocal of electrical conductivity=2.6×10$^{-4}$ Ω19 cm) as the blood coagulation-accelerating inorganic adsorbent, a methanolic dispersion was prepared to the respective concentrations of 0.1 weight % and 1.0 weight %. This dispersion was sprayed onto the inside wall of a 10 ml polypropylene blood sampling tube and dried to provide a blood test ware.

The amounts of deposition of the respective components per unit area of the inside wall surface of the tube were 2×10$^{-6}$ g/cm² for vinylpyrrolidone-vinyl acetate copolymer and 2×10$^{-5}$ g/cm² for finely divided silica.

Fresh human blood, 8 ml, was taken into the above blood test ware and allowed to stand at 20° C. The time till complete loss of fluidity of the blood was measured as blood coagulation time for assessment of clotting performance. After confirmation of coagulation, the sample was immediately centrifuged at 3000 rpm for 5 minutes and the serum separability was evaluated. At the same time, the supernatant was pipetted to find the serum yield. The results are shown in Table 1-4.

Example 2-2

Using the vinylpyrrolidone-vinyl acetate random copolymer (manufactured by BASF, Luviskol (tradename) VA28, vinyl acetate content ca 84 mol %) as the blood component deposition-preventing agent and the same finely divided silica as used in Example 2-1 as the blood coagulation accelerator, a methanolic dispersion was prepared to the respective concentrations of 0.02 weight % and 1.0 weight %. This dispersion was sprayed onto the inside wall of a 10 ml polypropylene blood sampling tube and dried to provide a blood test ware.

The amounts of deposition of the respective components per unit area of the inside wall surface of the tube were 5×10$^{-7}$ g/cm² for vinylpyrrolidone-vinyl acetate copolymer and 3×10$^{-5}$ g/cm² for finely divided silica.

Then, as in Example 2-1, clottability, serum separability, and serum yield were evaluated. The results are shown in Table 1-4.

Comparative Example 2-1

Using a vinylpyrrolidone homopolymer (manufactured by BASF, Luviskol(tradename) K30, weight average molecular weight 30000) as the blood component deposition-preventing agent and the same finely divided silica as used in Example 2-1 as tile blood coagulation accelerator, a methaniolic dispersion was prepared to the respective concentrations of 0.1 weight % and 1.0 weight %. This dispersion was spray-coated on the inside wall of a 10 ml polypropylene. blood sampling tube and air-dried to provide a blood test ware.

The amounts of deposition of the respective components per unit area of the inside wall surface of the tube were 3×10$^{-6}$ g/cm² for vinylpyrrolidone homopolymer and 3×10$^{-5}$ g/cm² for finely divided silica. Then, as in Example 2-1, clottability, serum separability, and serum yield were evaluated. The results are shown in Table 1-4.

Comparative Example 2-2

Using the same finely divided silica as used in Example 2-1 as the blood coagulation accelerator but not using a blood component deposition-preventing agent, a methanolic dispersion containing 1.0 weight % of silica was prepared. This dispersion was spray-coated on the inside wall of a 10 ml polypropylene blood sampling tube and air-dried to provide a blood test ware.

The amount of deposition of the above component per unit area of the inside wall surface of the ware was 3×10$^{-5}$ g/cm².

Then, as in Example 2-1, clottability, serum separability, and serum yield were evaluated. The results are shown in Table 1-4.

TABLE 1-4

|  | Blood coagulation time (min.) | Serum separability | Serum yield (ml) |
| --- | --- | --- | --- |
| Example 2-1 | 20 | good | 4.2 |
| Example 2-2 | 25 | good | 4.2 |
| Comparative Example 2-1 | 35 | poor | Not recovered |
| Comparative Example 2-2 | 40 | poor | Not recovered |

Example 2-1

Using the vinylpyrrolidone-vinyl acetate random copolymer (manufactured by BASF, Luviskol (tradename) VA64, vinyl acetate content ca 46 mol %) as the blood component deposition-preventing agent, an aqueous solution of 1.0 weight % concentration in pure water was prepared. On the other hand, using the same finely divided silica as used in Example 2-1 as the blood coagulation accelerator, an aqueous dispersion of 1.0 weight t concentration in pure water was prepared. About 50 µl of the aqueous solution of vinylpyrrolidone-vinyl acetate random copolymer was spray-coated on the inside wall of a polyethylene terephthalate) blood sampling tube of 10 ml capacity and dried in an air-current dryer at 60° C. Then, about 50 µl of the aqueous suspension of finely divided silica was further spray-coated and dried in an air-current dryer at 60° C. to provide a blood test ware. Fresh rabbit blood, 5 ml, was taken in this blood test ware and allowed to stand at the room temperature of 23 to 25° C. The time till loss of fluidity of the blood and start of separation of serum was measured as blood coagulation time. Then, at 1 hour after blood sampling and following centrifugation, the degree of adhesion of the blood clot to the inside wall of the blood test ware was visually evaluated and the serum yield determined as in Example 1-1. The results are shown in Table 1-5.

Then, to confirm the influence of the blood component deposition-preventing agent on immunoserological parameter values, the whole amount of the serum was transferred to a clean glass test tube immediately after completion of the above evaluation, Then, using HBs-Ab test reagent (manufactured by To a Medical Electronics Co., Ltd.) and Free T4 test reagent (manufactured by Kodak), HBs-Ab and Free T4 tests were performed on the serum for immunoserological assessment. The test results were not false positive but negative as shown in Table 1-5.

Example 3-2

Except that a 1.0 weight % aqueous solution of vinyl alcohol-acetate random copolymer (manufactured by Unitika Ltd., Unitika Poval (tradename) UMR-30L, vinyl acetate content ca 60 mol %) in pure water was used in lieu of a 1.0 weight % solution of vinylpyrrolidone-vinyl acetate random copolymer in pure water, a blood test ware was fabricated in otherwise the sate manner as in Example 3-1 and the tests described in Example 3-1 were carried out. The results are shown in Table 1-5.

Comparative Example 3-1

Except that the use of vinylpyrrolidone-vinyl acetate random copolymer was omitted, a blood test ware was fabricated in otherwise the same manner as in Example 3-1 (silica only was used), and the tests described in Example 3-1 were carried out. The results are shown in Table 1-5.

However, immunoserological tests could not be performed because the blood clot was not separable from the inside wall of the blood sampling tube so that the serum could not be recovered.

Comparative Example 3-2

Except that a plain hard glass blood sampling tube of 10 ml capacity in lieu of the blood test ware comprising a polyethylene terephthalate) blood sampling tube containing said vinylpyrrolidone-vinyl acetate random copolymer and silica, the same tests as described in Example 3-1 were performed. The results are shown in Table 1-5.

Comparative Example 3-3

Except that a 1.0 weight t solution of a polyether-modified silicone oil nonionic surfactant (manufactured bay Toray-Dow Corning Silicone, SH3749) in pure water in lieu of a solution of vinylpyrrolidone-vinyl acetate random copolymer in pure water, the procedure of Example 3-1 was otherwise repeated to provide a blood test ware and the tests described in Example 3-1 were carried out. The results are shown in Table 1-5.

TABLE 1-5

|  | Example | | Comparative Example | | |
|---|---|---|---|---|---|
|  | 3-1 | 3-2 | 3-1 | 3-2 | 3-3 |
| Blood coagulation time (min.) | 20 | 20 | 20 | 30 | 25 |
| Adhesion of clots at 1 hr after blood sampling | None | None | Significant adhesion | None | None |
| Adhesion of clots after centrifugation | None | None | Significant adhesion | None | None |
| Serum yield after centrifugation (ml) | 2.6 | 2.5 | 0.0 | 2.5 | 2.5 |
| HBs-Ab | Negative | Negative | No recovery of serum; | Negative | False positive |
| Free T4 | Negative | Negative | not tested | Negative | False positive |

The results of Examples 2-1 to 2-2 and 3-1 to 3-2, and Comparative Examples 2-1 to 2-2 and 3-1 to 3-3 indicate that compared with the case where the inside wall was not treated at all, the polypropylene blood sampling tube and polyethylene terephthalate blood sampling tube carrying only the blood coagulation accelerator silica spray-coated on the inside wall (Comparative Example2-2 and Comparative Example 3-1, respectively) suffer from more remarkable clot deposits and fail to permit recovery of serum, the use of the blood component deposition-preventing agent of the invention in combination with silica insures good serum separability without inhibiting the coagulation-accelerating action of silica.

Furthermore, the results of Examples 3-1 to 3-2 and Comparative Examples 3-1 to 3-3 indicate that whereas the blood component deposition-preventing agent of the present invention does not induce false positive tests for HBs-Ab and Free T4, the conventional nonionic surfactant give false positive tests.

Example 4-1

Using a vinylpyrrolidone-vinyl acetate random copolymer (manufactured by BASF, Luviskol(tradename) VA28, vinyl acetate content ca 84 mol %) as the blood component deposition-preventing agent, a methanolic solution of 0.02 weight % concentration was prepared, spray-coated on the inside wall of a polyethylene terephthalate (PET) tube of 10 ml capacity (16 mm in. dia.×100 mm long) and air-dried. The coating amount per unit area of the inside wall was $5 \times 10^{-7}$ g/cm$^2$ as vinylpyrrolidone-vinyl acetate random copolymer.

Then, a liquid dicyclopentadiene (DCPD) resin (manufactured by Exon (tradename) ECR-327), which is a plasma separator, was mixed with finely divided silica (manufactured by Japan Aerosil Co., (tradename) Aerosil A-200) under agitation to prepare a composition with a specific gravity of 1.05 and 1.2 g of the composition was put in the tube. Then, 120 U of heparin sodium as the blood anticoagulant was further accommodated to provide a blood test ware.

Fresh human blood, 8 ml, was put in the above blood test tube and the tube was stoppered and turned upside down 3 times for blending. The tube was then allowed to sit at 20°

C. for 10 minutes and, thereafter, centrifuged at 3000 rpm for 5 minutes to observe the separability of plasma. At the same time, ½ of the supernatant plasma was pipetted for use as a sample immediately after centrifugation.

Further, the blood test ware after centrifugation was stored at 40° C. for 24 hours and the supernatant plasma was pipetted to provide a 24-hour storage sample.

Using the above sample after centrifugation and the 24-hour storage sample, lactic dehydrogenase (LDH), creatine kinase (CPK) and potassium (K) concentrations were determined. The results are shown in Table 1-6. The measured values presented in Table 1-6 are the relative values with the value found for the sample immediately after centrifugation being taken as 100.

Comparative Example 4-1

A glass tube of 10 ml capacity (16 mm in. dia.×100 mm long) was charged with 120 U of heparin sodium as anticoagulant to provide a blood test ware (neither the vinylpyrrolidone-vinyl acetate random copolymer nor the plasma separator was used).

The performance evaluation of this blood test ware was carried out in the following manner. Thus, whereas the performance evaluation in Example 4-1 was made by "storing the blood test ware after centrifugation at 4° C. and pipetting the supernatant plasma again after 24 hours for use as a 24-hour storage sample", "the whole amount of the plasma was recovered from the blood test ware after centrifugation and ½ of the plasma was taken as a sample immediately after centrifugation, while the remainder was transferred to another glass tube and stored at 40° C. for 24 hours for use as a 24-hour storage sample". Otherwise the performance evaluation was made in the same manner as described in Example 4-1. The results are shown in Table 1-6.

Comparative Example 4-2

Except that the vinylpyrrolidone-vinyl acetate random copolymer was not used, the procedure of Example 4-1 was otherwise repeated to provide a blood test ware (this ware contained the plasma separator and blood anticoagulant). The performance evaluation of this blood test ware was carried out in the same manner as described in Example 4-1. The results are shown in Table 1-6.

TABLE 1-6

| | Separability of serum | Measured value | | |
|---|---|---|---|---|
| | | LDH | CPK | K |
| Example 4-1 | Good | 100 | 100 | 105 |
| Comparative Example 4-1 | Good | 100 | 100 | 100 |
| Comparative Example 4-2 | Poor | 120 | 130 | 110 |

Example 5-1

Using a vinylpyrrolidone-vinyl acetate random copolymer (manufactured by BASF, Luviskol (tradename) VA64, vinyl acetate content ca 46 mol %) as the blood component deposition-preventing agent and heparin lithium as the blood anticoagulant, a mixed solution containing 1.0 weights and 4000 IU/ml, respectively, of these substances in pure water was prepared. About 25 µl of this solution was spray-coated on the inside wall of a polyethylene terephthalate) blood sampling tube of 7 ml capacity and dried in an air-current dryer at 60° C. Then, about 1 g of a pasty serum/plasma separator (manufactured by Sekisui Kagaku Kogyo Kabustiki Kaisha, S-Collect (tradename)) was introduced into the bottom portion of the dried blood sampling tube to provide a blood test ware, This blood test ware was charged with 6 ml of fresh rabbit blood, turned upside down for through blending, and centrifuged (25° C.) at 1300 G for 5 minutes to visually evaluate the separability of plasma. Immediately then, about one-half volume of the plasma was transferred to a clean hard glass test tube (a sample for initial baseline values), while the remainder as contained in the poly(ethylene terephthalate) tube was stored in the refrigerator at 4° C. for 24 hours.

After 24 hours, the remaining plasma was transferred to a clean hard glass tube (a 24-hour storage sample for 24-hour values). Using the above two plasma samples taken in hard glass test tubes, the influences on blood chemistry parameters (LDH as an enzyme and K as an electrolyte) were investigated. The results are shown in Table 1-7.

Example 5-2

Except that a vinyl alcohol-vinyl acetate random copolymer (Unitika Ltd., Unitika Poval UMR-30L (tradename), vinyl acetate content ca. 60 mol %) was used in lieu of said vinylpyrrolidone-vinyl acetate random copolymer, the procedure of Example 5-1 was otherwise repeated to provide a blood test ware and using the ware, tests were performed as in Example 5-1. The results are shown in Table 1-7.

Comparative Example 5-1

Except that the use of vinylpyrrolidone-vinyl acetate random copolymer as the blood component deposition-preventing agent was omitted, the procedure of Example 5-1 was otherwise repeated to provide a blood test ware (the heparin lithium and serum/plasma separator were used). Using this blood test ware, the same tests were performed as in Example 5-1. The results are shown in Table 1-7.

Comparative Example 5-2

The inside wall of a clean hard glass blood sampling tube of 7 ml capacity was spray-coated with about 25 µl of a solution containing 4000 IU/ml of heparin lithium in pure water and dried in an air-current dryer at 60° C. to prepare a blood test ware (the serum/plasma separator was not introduced). This blood test tube was charged with 6 ml of fresh rabbit blood, turned upside down a sufficient times for blending, and centrifuged (25° C.) at 1300 G for 5 minutes to evaluate plasma separability after centrifugation as in Example 5-1. Immediately then the whole amount of plasma was transferred to another clean hard glass test tube (a sample for initial baseline values) and stored in the refrigerator at 4° C. for 24 hours. After 24 hours, the same tests as in Example 5-1 were performed. The results are shown in Table 1-7.

TABLE 1-7

| | | Example | | Comparative Example | |
|---|---|---|---|---|---|
| | | 5-1 | 5-2 | 5-1 | 5-2 |
| Adhesion of blood components after centrifugation | | None | None | Adhesion of platelets | None |
| LDH(IU/L) | Initial | 123 | 129 | 120 | 123 |
| | After 24 hr of standing | 119 | 121 | 305 | — |

TABLE 1-7-continued

|   |   | Example |   | Comparative Example |   |
|---|---|---|---|---|---|
|   |   | 5-1 | 5-2 | 5-1 | 5-2 |
| K (mEq/L) | Initial | 4.0 | 4.0 | 4.1 | 4.0 |
|   | After 24 hr of standing | 4.3 | 4.5 | 5.3 | — |

The results of Examples 5-1 to 5-2 and Comparative Examples 5-1 to 5-2 indicate that the poly(ethylene terephthalate) blood sampling tube carrying a spray-coated anticoagulant heparin salt on its inside wall showed deposits of platelets and because of the leakage of LDH and K from the platelets during storage at 40° C., the corresponding parameter values are elevated. In Contrast, the blood component deposition-preventing agent of the present invention effectively prevented deposition of platelets, thus insuring stability of such parameter values. Similar findings were also obtained between Example 4-1 and Comparative Examples 4-1 and 4-2.

Example 6-1

Using a vinylpyrrolidone-vinyl acetate random copolymer (manufactured by BASF, Luviskol TM VA64, vinyl acetate content ca 46 mol %) as the blood component deposition-preventing agent and the same finely divided silica as used in Example 2-1 as the blood coagulation accelerator, a suspension containing 1.0 weight % and 2.0 weight % of the respective substances in methanol was prepared. This suspension was used to coat polystyrene pellets having a diameter of about 3 mm in an explosion-proof air-current dryer at 60° C. under agitation and dried to provide a blood component deposition-preventing matrix. The amounts of deposition of the respective substances on the surface of pellets were about $2 \times 10^{-5}$ g/cm$^2$ for vinylpyrrolidone-vinyl acetate random copolymer and about $7 \times 10^{-7}$ g/cm$^2$ for finely divided silica.

A clean hard glass blood sampling tube of 10 ml capacity was charged with 0.6 g of the above blood component deposition-preventing matrix to provide a blood test ware. This blood test ware was charged with 4 ml of fresh rabbit blood and allowed to sit at the room temperature of 23 to 25° C. After measurement of blood coagulation time, the sample was centrifuged (25° C.) at 1300° C. for 5 minutes to visually evaluate serum separability and the serum yield was determined. As a result, although the pellets were found scatteredly buried near the head of the clot, a clean serum without showing signs of hemolysis was obtained. The coagulation time and serum yield values are shown in Table 1-8.

Comparative Example 6-1

Except that the use of vinylpyrrolidone-vinyl acetate random copolymer was omitted, the procedure of Example 6-1 was otherwise repeated to prepare silica powder-coated polystyrene pellets. The amount of deposition of finely divided silica was about $5 \times 10^{-5}$ g/cm$^2$. A clean hard glass blood sampling tube of 10 ml capacity was filled with 0.6 g of the coated polystyrene pellets to provide a blood test ware. This blood test ware was charged with 4 ml of fresh rabbit blood and the blood coagulation time, serum separability, and serum yield were determined as in Example 6-1. As a result, the pellets were found buried near the head of the clot as in Example 6-1. The serum yield was as good as that obtained in Example 6-1 but marked hemolysis was observed. The coagulation time and serum yield values are presented in Table 1-8.

Comparative Example 6-2

A clean hard glass blood sampling tube of 10 ml capacity was charged with 0.6 g of uncoated polystyrene pellets to provide a blood test ware. This blood test ware was filled with 4 ml of fresh rabbit blood and the blood coagulation time, serum separability, and serum yield were determined as in Example 6-1. As a result, the pellets were found buried near the head of the clot as in Example 6-1. The serum yield was as good as that obtained in Example 6-1 but marked hemolysis was observed. The coagulation time and serum yield values are presented in Table 1-8.

TABLE 1-8

|   | Blood coagulation time (min.) | Separability of serum | Serum yield (ml) |
|---|---|---|---|
| Example 6-1 | 20 | Good | 2.2 |
| Comparative Example 6-1 | 20 | Very remarkable hemolysis | 2.0 |
| Comparative Example 6-2 | 45 | Remarkable hemolysis | 2.1 |

Examples 7-1 to 7-12 and Comparative Example 7-1

Confirmation of Antimicrobial Activity

Blood coagulation accelerator suspensions in pure water were prepared according to the formulas shown in Table 2-1 In Table 2-1, Bactekiller means BM103A manufactured by Kanebo, Ltd., Ice means NAZ320 manufactured by Catalysts & Chemicals Industries Co., Ltd., Rasap means AN600 manufactured by Rasa Industries, Ltd., and Novalon means AG300 manufactured by Toa Gosei Chemical Industry Co., Ltd.

Separately, a suspension of silica powder (1.0%) and polyvinylpyrrolidone (2.0%) in pure water was prepared and exposed to interior air for microbial contamination for use as an inoculum. Using the suspensions according to Table 2-1 as they were and the corresponding suspensions obtained by inoculation with seed microorganisms and subsequent 10 hours of agitation, bacterial and fungal culture assays were carried out in the routine manner. The media and cultural conditions were as follows. For bacteria, culture was carried out using Standard Method Agar at 30° C. for 3 days. The inoculum size of each suspension was set at 0.3 ml. For fungi, culture was carried out using Potato Dextrose Agar at 25° C. for 5 days. The inoculum size of each suspension for fungal assays was 0.3 ml. The frequency of colonies on each medium was recorded. the results for the media used in the culture of bacteria and fungi are shown in Table 2-2 and Table 2-3, respectively. In each table, – means no colony formation and +++ means formation of many colonies.

Examples 7-13 to 7-20

Confirmation of Influences on Blood Coagulation

Blood coagulation accelerator suspensions in pure water were prepared according to the formulas shown in Table 2-4. About 50 µl of each suspension was spray-coated on a poly(methyl methacrylate) blood sampling tube of 10 ml capacity and dried in an air-current dryer at 60° C. Then, fresh rabbit blood, 3 ml, was drawn into each blood sampling tube and allowed to stand at the room temperature of 23 to 25° C. The time till the blood lost fluidity and the serum began to seep out was measured as blood coagulation time. The results are shown in Table 2-5.

Examples 7-11 to 7-28

Confirmation of Influences on Blood Examination Parameter Values

After completion of the evaluation described in Examples 7-13 to 7-20, each sample was centrifuged at 1800 G for 5 minutes to recover the serum. Using the serum, influence on representative biochemical parameters (GOT and ALP as enzymes, TG, PL and T-CHO as lipids, and Na, K, Cl, Mg, and Ca as electrolytes, and Fe and Cu as metals) were investigated. The results are presented in Table 2-6. In Table 2-6, the blood sampling tubes of Example 7-21 to 7-28 correspond to the blood sampling tubes of examples 7-13 to 7-20, respectively.

Comparative Examples 7-2 to 7-4

A blood coagulation accelerator suspension in pure water which contained no antimicrobial composition was prepared according to the formula shown in Table 2-4. About 50 μl of this suspension was spray-coated on a poly(methyl methacrylate) blood sampling tube of 10 ml capacity and dried in an air-current dryer at 60° C. (Comparative Example 7-2). Separately, a 10 ml hard glass blood sampling tube not spray-coated with the blood coagulation accelerator (Comparative Example 7-3) and a similar poly(methyl methacrylate) blood sampling tube (Comparative Example 7-4) were provided. Fresh rabbit blood was drawn into these 3 different blood sampling tubes and the blood coagulation times were determined in the manner described in Example 7-13. The results are shown alongside the results for Examples 7-13 to 7-20 in Table 2-5.

Comparative Example 7-5 to 7-7

After completion of the evaluation described in Comparative Examples 7-2 to 7-4, each sample was centrifuged at 1800 G for 5 minutes to recover the serum and, using the serum, the influences on biochemical parameter values were investigated. The results are shown alongside the results for Examples 7-21 to 7-28 in Table 2-6. In Table 2-6, the blood sampling tubes of Comparative Examples 7-5 to 7-7 correspond to the blood sampling tubes of Comparative Examples 7-2 to 7-4, respectively.

It will be apparent from the results shown in Table 2-2 and Table 2-3 that when a germ-free coagulation accelerator suspension immediately after preparation was contaminated by microorganisms, the microorganisms were ready to multiply in the absence of an antimicrobial composition (Comparative Example 7-1) but in cases where an antimicrobial composition was contained (Examples 7-1 to 7-12), invariably no colonies were detected, indicating that the invading microorganisms were destroyed.

The results shown in Table 2-5 indicate that it took more than 1 hour for the blood to be coagulated in the plain poly(methyl methacrylate) blood sampling tube not treated with a coagulation accelerator (Comparative Example 7-4) but coagulation was completed within 20 to 30 minutes in the presence of the blood coagulation accelerator according to the present invention (Examples 7-13 to 7-20). The latter result is fully comparable not only to the result with the conventional coagulation accelerator in the absence of an antimicrobial composition (Comparative Example 7-2) but also to the result with the hard glass blood sampling tube (Comparative Example 7-3), indicating that the antimicrobial composition of the present invention does not interfere with blood coagulation but rather has positive coagulation accelerating activity.

The results shown in Table 2-6 indicate that none of the antimicrobial compositions had any remarkable confounding effects on blood parameter values.

TABLE 2-1

|  | Antimicrobial composition (%) | | | | Coagulation accelerator (%) | Binder (%) Polyvinyl- |
|---|---|---|---|---|---|---|
|  | Bactekiller | Ice | Rasap | Novarone | Silica | pyrrolidone |
| Example 7-1 | 0.10 | — | — | — | 1.0 | 2.0 |
| Example 7-2 | 0.50 | — | — | — | 1.0 | 2.0 |
| Example 7-3 | 1.00 | — | — | — | 1.0 | 2.0 |
| Example 7-4 | — | 0.10 | — | — | 1.0 | 2.0 |
| Example 7-5 | — | 0.50 | — | — | 1.0 | 2.0 |
| Example 7-6 | — | 1.00 | — | — | 1.0 | 2.0 |
| Example 7-7 | — | — | 0.10 | — | 1.0 | 2.0 |
| Example 7-8 | — | — | 0.50 | — | 1.0 | 2.0 |
| Example 7-9 | — | — | 1.00 | — | 1.0 | 2.0 |
| Example 7-10 | — | — | — | 0.10 | 1.0 | 2.0 |
| Example 7-11 | — | — | — | 0.50 | 1.0 | 2.0 |
| Example 7-12 | — | — | — | 1.00 | 1.0 | 2.0 |
| Comparative Example 7-1 | — | — | — | — | 1.0 | 2.0 |

TABLE 2-2

|  | Example | | | | | | | | | | | | Comparative Example |
|---|---|---|---|---|---|---|---|---|---|---|---|---|---|
|  | 7-1 | 7-2 | 7-3 | 7-4 | 7-5 | 7-6 | 7-7 | 7-8 | 7-9 | 7-10 | 7-11 | 7-12 | 7-1 |
| Suspension | − | − | − | − | − | − | − | − | − | − | − | − | − |
| Inoculated suspension | − | − | − | − | − | − | − | − | − | − | − | − | +++ |

TABLE 2-3

|  | Example |  |  |  |  |  |  |  |  |  |  |  | Comparative Example |
|---|---|---|---|---|---|---|---|---|---|---|---|---|---|
|  | 7-1 | 7-2 | 7-3 | 7-4 | 7-5 | 7-6 | 7-7 | 7-8 | 7-9 | 7-10 | 7-11 | 7-12 | 7-1 |
| Suspension | − | − | − | − | − | − | − | − | − | − | − | − | − |
| Inoculated suspension | − | − | − | − | − | − | − | − | − | − | − | − | +++ |

TABLE 2-4

|  | Antimicrobial composition (%) | | | | Coagulation accelerator (%) | Binder (%) Polyvinyl- |
|---|---|---|---|---|---|---|
|  | Bactekiller | Ice | Rasap | Novarone | Silica | pyrrolidone |
| Example 7-13 | 0.10 | — | — | — | 0.9 | 2.0 |
| Example 7-14 | 1.00 | — | — | — | — | 2.0 |
| Example 7-15 | — | 0.10 | — | — | 0.9 | 2.0 |
| Example 7-16 | — | 1.00 | — | — | — | 2.0 |
| Example 7-17 | — | — | 0.10 | — | 0.9 | 2.0 |
| Example 7-18 | — | — | 1.00 | — | — | 2.0 |
| Example 7-19 | — | — | — | 0.10 | 0.9 | 2.0 |
| Example 7-20 | — | — | — | 1.00 | — | 2.0 |
| Comparative Example 7-2 to 7-4 | — | — | — | — | 1.0 | 2.0 |

TABLE 2-5

|  | Example | | | | | | | | Comparative Example | | |
|---|---|---|---|---|---|---|---|---|---|---|---|
|  | 7-13 | 7-14 | 7-15 | 7-16 | 7-17 | 7-18 | 7-19 | 7-20 | 7-2 | 7-3 | 7-4 |
| Blood coagulation time (min.) | 30 | 30 | 20 | 20 | 25 | 30 | 20 | 30 | 20 | 25 | 85 |

TABLE 2-6

|  | Example | | | | | | | | Comparative Example | | |
|---|---|---|---|---|---|---|---|---|---|---|---|
|  | 7-21 | 7-22 | 7-23 | 7-24 | 7-25 | 7-26 | 7-27 | 7-28 | 7-5 | 7-6 | 7-7 |
| GOT (IU/l) | 167 | 164 | 168 | 165 | 159 | 171 | 174 | 162 | 169 | 173 | 165 |
| ALP (IU/l) | 101 | 102 | 100 | 102 | 98 | 100 | 101 | 100 | 99 | 101 | 98 |
| TG (mg/dl) | 56 | 53 | 56 | 52 | 53 | 55 | 54 | 50 | 53 | 54 | 52 |
| PL (mg/dl) | 51 | 50 | 50 | 49 | 49 | 50 | 49 | 49 | 50 | 50 | 49 |
| T-CHO (mg/dl) | 16 | 16 | 16 | 16 | 16 | 16 | 16 | 16 | 16 | 16 | 16 |
| Na (mEq/l) | 146 | 149 | 148 | 146 | 148 | 148 | 146 | 150 | 149 | 146 | 147 |
| K (mEq/l) | 5.0 | 5.0 | 5.2 | 5.0 | 5.0 | 5.3 | 4.9 | 5.3 | 5.1 | 4.9 | 4.9 |
| Cl (mEq/l) | 98 | 101 | 100 | 101 | 100 | 102 | 98 | 101 | 98 | 100 | 100 |
| Mg (mg/dl) | 4.1 | 4.1 | 4.0 | 4.2 | 4.0 | 4.1 | 4.1 | 4.0 | 4.1 | 4.0 | 4.0 |
| Ca (mg/dl) | 13.9 | 13.7 | 13.9 | 13.5 | 13.9 | 14.1 | 14.2 | 14.1 | 13.9 | 14.2 | 14.1 |
| Fe ($\mu$g/dl) | 217 | 213 | 218 | 216 | 215 | 211 | 213 | 214 | 208 | 213 | 215 |
| Cu ($\mu$g/dl) | 152 | 145 | 146 | 146 | 150 | 147 | 145 | 147 | 150 | 145 | 147 |

Example 1

Using a polyvinylpyrrolidone (manufactured by BASF, tradename Luviskol K80, K value 80, weight average molecular weight ca 800000), a dispersion of 0.1 weight % concentration in methanol was prepared. This dispersion was spray-coated on the inside wall of a poly(ethylene terephthalate) (PET) tube of 10 ml capacity (16 mm in. dia.×100 mm long) and air-dried. The coating amount per unit area of the inside wall of the tube was $2 \times 10^{-6}$ g/cm$^2$ as polyvinylpyrrolidone.

Further, as the plasma separator, dicyclopentadiene (DCPD) resin (manufactured by Exon tradename ECR-327) was mixed with finely divided silica (manufactured by Japan Aerosil Co., tradename Aerosil A-200) to prepare a composition with a specific gravity of 1.05 and 1.2 g of the composition was introduced into the above tube. Then, 120 U of heparin sodium as blood anticoagulant was further introduced to provide a blood test ware.

Example 2

Using a polyvinylpyrrolidone (manufactured by BASF, tradename Luviskol K90, K value 90, weight average molecular weight ca 1100000), a dispersion of 0.02 weight % concentration in methanol was prepared and this dispersion was spray-coated on the inside wall of a PET tube similar to the tube used in Example 1 and air-dried. The coating amount per unit area of the inside wall was $6 \times 10^{-7}$ g/cm$^2$ as polyvinylpyrrolidone. Thereafter, the plasma separator and the blood anticoagulant were introduced as in Example 1 to provide a blood test ware.

Comparative Example 1

A glass tube of 10 ml capacity (16 mm in. dia.×100 mm long) was charged with 120 U of heparin sodium as a blood anticoagulant to provide a blood test ware (neither polyvinylpyrrolidone nor a plasma separator was used).

Comparative Example 2

Except that the use of polyvinylpyrrolidone was omitted, the procedure of Example 1 was repeated to provide a blood test ware (the plasma separator and the anticoagulant were used).

Performance Evaluation

The relative performance of the blood test wares according to Examples 1 and 2-and Comparative Example 2 was evaluated as follows.

Fresh human blood, 8 ml, was drawn into each blood test ware and stoppered tight. The ware was turned upside down 3 times for blending, then allowed to sit at 20° C. for 10 minutes, and centrifuged at 3000 rpm for 5 minutes to assess plasma separability. At the same time, ½ of the supernatant plasma was quickly pipetted as a sample immediately after centrifugation.

The same centrifuged blood test ware was stored at 4° C. for 24 hours and the supernatant plasma was pipetted again for use as a 24-hour storage sample.

Using the above sample immediately after centrifugation and 24-hour storage sample, lactic dehydrogenase (LDH), creatine kinase (CPK) and potassium (K) were assayed immediately after centrifugation for the former sample and at 24 hours after centrifugation for the latter 24-hour storage sample. The values found are presented in Table 1. The assay method was the lactic substrate method for LDH, the creatine phosphate substrate method for CPK, and flame photometry for K. The measured values shown in Table 1 are relative values with the values found for the sample immediately after centrifugation being taken as 100.

The performance evaluation of the blood test ware of Comparative Example 1 was carried out in the same manner as above, except that whereas the performance evaluation in Example 4-1 was made by "storing the blood test ware after centrifugation at 4° C. and pipetting the supernatant plasma again after 24 hours for use as a 24-hour storage sample", "the plasma recovered from the blood test ware immediately after centrifugation was transferred to another glass tube and stored at 4° C. for 24 hours and the supernatant plasma was used as a 24-hour storage sample".

TABLE 1

| | Separability of serum | Measured value | | |
|---|---|---|---|---|
| | | LDH | CPK | K |
| Example 1 | Good | 105 | 105 | 100 |
| Example 2 | Good | 105 | 105 | 105 |
| Comparative Example 1 | Good | 100 | 100 | 100 |
| Comparative Example 2 | Poor | 120 | 130 | 110 |

Examples 3 to 8 and Comparative Examples 3 and 4

Aqueous solutions each containing both polyvinylpyrrolidone and heparin sodium at the concentrations indicated in Table 2 were prepared. Each of these aqueous solutions was spray-coated on the inside wall of a PET tube similar to the one used in Example 1 and dried. The coating amounts of polyvinylpyrrolidone and heparin sodium per unit area of the inside wall are shown in Table 2.

The vinylpyrrolidone polymers shown in table 2 are invariably the products of BASF and the correspondence between the indicated weight average molecular weight and the tradename are: ca 50000=Luviskol K30, ca 350000 =Luviskol K60, ca 800000=Luviskol K80, and ca 1100000= Luviskol K90.

Then, the plasma separator was introduced as in Example 1 to provide blood test wares.

Comparative Example 5

An aqueous solution containing 4500 U/ml of heparin sodium, 20 μl, as a blood anticoagulant was spray-coated on the inside wall of a glass tube of 10 ml capacity (16 mm in. dia.×100 mm long) and dried to provide a blood test ware. The coating amount, as heparin sodium, per unit area of the inside wall of the tube is shown in Table 2.

Performance Evaluation

The relative performance of the blood test wares according to Examples 3 to 8 and Comparative Examples 3 to 5 was evaluated as follows.

Fresh human blood, 3 ml, was drawn into each blood test ware and stoppered tight. The ware was turned upside down 3 times for blending, then allowed to sit at 20° C. for 10 minutes, and centrifuged at 3000 rpm for 5 minutes to assess plasma separability. The results are shown in Table 3.

Then, ½ of the supernatant plasma was taken, transferred to a fresh clean hard glass blood sampling tube, and stored frozen as a sample immediately after centrifugation.

The remaining plasma in the blood test ware was stored as it was at 4° C. for 24 hours. Then, it was transferred to a fresh clean hard glass blood sampling tube and stored frozen for use as a 24-hour storage sample.

As to the blood test ware prepared in Comparative Example 5, the plasma separability was evaluated and, then, the whole amount of supernatant plasma was transferred to a fresh clean hard glass blood sampling tube and stored frozen for use as a sample immediately after centrifugation.

All the frozen samples were thawed 48 hours later and the concentrations of lactic dehydrogenase (LDH), creatine kinase (CPK) and potassium (K) were determined as in Example 1. The results are presented in Table 3. The values given in Table 3 are the measured values.

TABLE 2

| | | Polyvinylpyrrolidone | | | Heparin sodium | |
|---|---|---|---|---|---|---|
| | K | Weight average molecular weight | Concentration (wt %) | Amount of deposits (g/cm$^2$) | Concentration (U/ml) | Amount of deposits (U/cm$^2$) |
| Example 3 | 60 | ca 35 × 10$^4$ | 0.1 | 3 × 10$^{-7}$ | 4500 | 1.4 |
| Example 4 | 60 | ca 35 × 10$^4$ | 5.0 | 2 × 10$^{-5}$ | 4500 | 1.9 |
| Example 5 | 80 | ca 80 × 10$^4$ | 0.1 | 1 × 10$^{-6}$ | 4500 | 4.8 |
| Example 6 | 80 | ca 80 × 10$^4$ | 5.0 | 4 × 10$^{-5}$ | 4500 | 3.4 |
| Example 7 | 90 | ca 110 × 10$^4$ | 0.1 | 9 × 10$^{-7}$ | 4500 | 3.8 |
| Example 8 | 90 | ca 110 × 10$^4$ | 5.0 | 7 × 10$^{-5}$ | 4500 | 6.3 |
| Comparative Example 3 | 30 | ca 5 × 10$^4$ | 0.1 | 4 × 10$^{-7}$ | 4500 | 1.9 |
| Comparative Example 4 | 30 | ca 5 × 10$^4$ | 5.0 | 4 × 10$^{-5}$ | 4500 | 3.4 |
| Comparative Example 5 | — | — | — | — | 4500 | 2.0 |

TABLE 3

| | Separability of plasma | LDH (IU/l) | | CPK (IU/l) | | K (mEq/l) | |
|---|---|---|---|---|---|---|---|
| | | Immediately after separation | After 24 hr | Immediately after separation | After 24 hr | Immediately after separation | After 24 hr |
| Example 3 | ○ | 200 | 200 | 103 | 93 | 3.8 | 3.9 |
| Example 4 | ○ | 205 | 201 | 101 | 102 | 3.8 | 4.1 |
| Example 5 | ○ | 198 | 204 | 105 | 104 | 3.9 | 4.0 |
| Example 6 | ○ | 205 | 210 | 102 | 105 | 3.9 | 4.0 |
| Example 7 | ○ | 208 | 201 | 109 | 107 | 3.9 | 4.0 |
| Example 8 | ○ | 200 | 201 | 99 | 102 | 3.8 | 4.0 |
| Comparative Example 3 | x | 204 | 238 | 98 | 119 | 4.0 | 4.9 |
| Comparative Example 4 | x | 201 | 254 | 100 | 123 | 3.9 | 5.2 |
| Comparative Example 5 | ○ | 204 | — | 101 | — | 4.0 | — |

In the plasma separability column of Table 3, ○ denotes good and X denotes marked deposition of platelets.
Examples 9 to 24 and Comparative Examples 6 to 9

The formulas for the compositions coated on the inside walls of blood sampling tubes are shown in Table 4. In Table 4, Luviskol K80 means a grade of polyvinylpyrrolidone (κ value 80, weight average molecular weight ca 800000) manufactured by BASF, Luviskol K90 means a grade of polyvinylpyrrolidone (K value 90, weight average molecular weight ca 1100000) manufactured by BASF, EDTA2K means dipotassium ethylenediaminetetraacetate (manufactured by Wako Pure Chemical Industries, Ltd., reagent grade), Heparin Li means a reagent grade product of Sigma Chemical Company, and PMMA powder means a poly(methyl methacrylate) powder having a particle diameter of about 50 μm (MB-50, manufactured by Sekisui Kagaku Kogyo Kabushaiki Kaisha), and Cellulose powder means a finely divided cellulose having a particle diameter of about 20 μm (reagent grade, manufactured by Aldrich Chemical Company, Inc.).

TABLE 4

| | Polyvinyl-pyrrolidone | Blood anticoagulant | Finely divided insoluble powder |
|---|---|---|---|
| Example 9 | Luviskol K80 (0.1 w/w %) | EDTA2K (10 w/w %) | PMMA powder (0.1 w/w %) |
| Example 10 | Luviskol K80 (0.1 w/w %) | EDTA2K (10 w/w %) | Cellulose powder (0.1 w/w %) |
| Example 11 | Luviskol K80 (0.1 w/w %) | EDTA2K (10 w/w %) | PMMA powder (5.0 w/w %) |
| Example 12 | Luviskol K80 (0.1 w/w %) | EDTA2K (10 w/w %) | Cellulose powder (5.0 w/w %) |
| Example 13 | Luviskol K90 (0.1 w/w %) | EDTA2K (10 w/w %) | PMMA powder (5.0 w/w %) |
| Example 14 | Luviskol K90 (0.1 w/w %) | EDTA2K (10 w/w %) | Cellulose powder (5.0 w/w %) |
| Example 15 | Luviskol K90 (0.1 w/w %) | EDTA2K (10 w/w %) | PMMA powder (0.1 w/w %) |
| Example 16 | Luviskol K90 (0.1 w/w %) | EDTA2K (10 w/w %) | Cellulose powder (0.1 w/w %) |
| Example 17 | Luviskol K80 (0.1 w/w %) | Heparin Li (1000 IU/ml) | PMMA powder (0.1 w/w %) |
| Example 18 | Luviskol K80 (0.1 w/w %) | Heparin Li (1000 IU/ml) | Cellulose powder (0.1 w/w %) |
| Example 19 | Luviskol K80 (0.1 w/w %) | Heparin Li (1000 IU/ml) | PMMA powder (5.0 w/w %) |
| Example 20 | Luviskol K80 (0.1 w/w %) | Heparin Li (1000 IU/ml) | Cellulose powder (5.0 w/w %) |
| Example 21 | Luviskol K90 (0.1 w/w %) | Heparin Li (1000 IU/ml) | PMMA powder (0.1 w/w %) |
| Example 22 | Luviskol K90 (0.1 w/w %) | Heparin Li (1000 IU/ml) | Cellulose powder (0.1 w/w %) |
| Example 23 | Luviskol K90 (0.1 w/w %) | Heparin Li (1000 IU/ml) | PMMA powder (5.0 w/w %) |
| Example 24 | Luviskol K90 (0.1 w/w %) | Heparin Li (1000 IU/ml) | Cellulose powder (5.0 w/w %) |
| Comparative Example 6 | Luviskol K80 (0.1 w/w %) | EDTA2K (10 w/w %) | Not used |
| Comparative Example 7 | Luviskol K90 (0.1 w/w %) | EDTA2K (10 w/w %) | Not used |

TABLE 4-continued

|  | Polyvinyl-pyrrolidone | Blood anticoagulant | Finely divided insoluble powder |
|---|---|---|---|
| Comparative Example 8 | Luviskol K80 (0.1 w/w %) | Heparin Li (1000 IU/ml) | Not used |
| Comparative Example 9 | Luviskol K90 (0.1 w/w %) | Heparin Li (1000 IU/ml) | Not used |

Aqueous suspensions of the respective compositions according to Examples 9 to 24 or aqueous solutions of the respective compositions according to Comparative Examples 6 to 9 were prepared and about 30 μl of each suspension or solution was spray-coated on the inside wall of a poly(ethylene terephthalate) blood sampling tube of 7 ml capacity. The tubes were then allowed to sit in the upright position at 600° C. overnight to dry. Then, the retentivity of each composition on the inside wall of the tube was visually evaluated. The results are shown in Table 5. The results of these Examples and Comparative Examples indicate that the concomitant use of a finely divided insoluble powder results in a marked improvement in the retentivity of the suspension or solution on the inside wall of the tube.

TABLE 5

| Example | 9 | 10 | 11 | 12 | 13 | 14 | 15 | 16 |
|---|---|---|---|---|---|---|---|---|
| Retentivity | Good | Good | Good | Good | Good | Good | Good | Good |
| Example | 17 | 18 | 19 | 20 | 21 | 22 | 23 | 24 |
| Retentivity | Good | Good | Good | Good | Good | Good | Good | Good |
| Comparative Example | 6 | 7 | 8 | 9 |  |  |  |  |
| Retentivity | Marked sagging | Marked sagging | Marked sagging | Marked sagging |  |  |  |  |

Then, a plasma separator (S-Collect, Sekisui Kagaku Kogyo Kabushiki Kaisha), 0.9 g/tube, was introduced into all the blood sampling tube.

Then, 3 ml/tube of fresh rabbit blood was drawn into all the blood sampling tubes, which were then inverted once for gentle bending. The tubes were then allowed to sit at the room temperature of about 23° C. for 30 minutes. Thereafter, each tube was centrifuged at 1300 G for 5 minutes and immediately the deposition status of solid elements of blood on the inside wall above the plasma separator partition was visually evaluated. The results are shown in Table 6. Because of the intentional insufficient blending, Comparative Examples in which most of the composition was buried in the plasma separator failed to show adequate anticoagulation effects with small amounts of the clot adhering to the tube in a ring fashion at the liquid level. In the Examples, however, satisfactory anticoagulation effects were obtained.

TABLE 6

| Example | 9 | 10 | 11 | 12 | 13 |  |
|---|---|---|---|---|---|---|
| Retentivity | No adhesion | No adhesion | No adhesion | No adhesion | No adhesion |  |
| Example | 14 | 15 | 16 | 17 | 18 |  |
| Retentivity | No adhesion | No adhesion | No adhesion | No adhesion | No adhesion |  |
| Example | 19 | 20 | 21 | 22 | 23 | 24 |
| Retentivity | No adhesion | No adhesion | No adhesion | No adhesion | No adhesion | No adhesion |
| Comparative Example | 6 | 7 | 8 | 9 |  |  |
| Retentivity | A small amount of clot adhered in ring form at liquid level | A small amount of clot adhered in ring form at liquid level | A small amount of clot adhered in ring form at liquid level | A small amount of clot adhered in ring form at liquid level |  |  |

Then, from each of the blood sampling tubes, one-half of the plasma was taken (initial baseline samples) and stored frozen at −20° C. in a 5 ml poly(ethylene terephthalate) tube. The remaining one half of plasma was stored as it was at 4° C. for 20 hours and, then, stored frozen in a 5 ml poly(ethylene terephthalate) tube (20-hour storage samples) in the same manner.

Forty-eight (48) hours after blood sampling, β-TG was assayed in Examples 9 to 16 and Comparative Examples 6 and 7 and LDH and K were assayed in Examples 17 to 24 and Comparative Examples 8 and 9. The results are shown in Table 7. While β-TG is a substance contained at a high concentration in the platelets and LDH and K+ are substances contained at high concentrations in both the platelets and erythrocytes, these substances are released when the blood cells are stimulated or destroyed. In the Examples wherein a sufficient amount of the composition was retained on the inside wall of the tube, there was no deposition of blood cells on the inside wall so that the measured values after 24 hours of storage were not much different from the initial baseline values prior to storage. In the Comparative Examples, in which small amounts of the clot were found adhering to the inside wall, β-TG showed higher values, both initially and after 20 hours of storage, than in the Examples and LDU and K+showed upward changes in the course of 20 hours' storage.

TABLE 7

| | β-TG (ng/ml) | |
| --- | --- | --- |
| | Initial sample | Sample after 20 hr of standing |
| Example 9 | 15 | 16 |
| Example 10 | 15 | 16 |
| Example 11 | 14 | 15 |
| Example 12 | 13 | 15 |
| Example 13 | 17 | 15 |
| Example 14 | 15 | 13 |
| Example 15 | 17 | 17 |
| Example 16 | 16 | 15 |
| Comparative Example 6 | 21 | 43 |
| Comparative Example 7 | 25 | 47 |

TABLE 7-continued

| | LDH (IU/l) | | K (mEq/l) | |
| --- | --- | --- | --- | --- |
| | Initial sample | Sample after 20 hr of standing | Initial sample | Sample after 20 hr of standing |
| Example 17 | 105 | 107 | 4.1 | 4.1 |
| Example 18 | 107 | 105 | 4.1 | 4.1 |
| Example 19 | 106 | 103 | 4.0 | 4.1 |
| Example 20 | 103 | 105 | 4.0 | 4.1 |
| Example 21 | 105 | 107 | 4.0 | 4.1 |
| Example 22 | 104 | 101 | 4.0 | 4.1 |
| Exanple 23 | 103 | 108 | 4.0 | 4.1 |
| Example 24 | 107 | 105 | 4.0 | 4.1 |
| Comparative Example 8 | 105 | 138 | 4.1 | 5.8 |
| Comparative Example 9 | 109 | 154 | 4.1 | 6.1 |

Examples 25 to 40 and Comparative Examples 10 to 13

The formulas for the compositions coated on the inside walls of blood sampling tubes are shown in Table 8. In Table 8, VA64 means the random copolymer Luviskol VA64 manufactured by BASF (the monomer component giving a water-soluble homopolymer=46 mol % (40 weight %)), UMR-30L means the random copolymer Unitika Poval UMR-30L manufactured by Unitika Ltd. (the monomer component giving a water-soluble homopolymer=60 ml %), EDTA2K means dipotassium ethylenediaminetetraacetate (Wako Pure Chemical Industries, Ltd., reagent grade), Heparin Li means the corresponding reagent grade manufactured by Sigma Chemical Company, PMMA powder means a poly(methyl methacrylate) powder having a particle diameter of about 50 μm (MB-50, manufactured by Sekisui Kagaku Kogyo Kabushiki Kaisha), and Cellulose powder means a finely divided cellulose having a particle diameter of about 20 μm (reagent grade, Aldrich Chemical Company, Inc.).

TABLE 8

| | Random copolymer | Blood anticoagulant | Finely divided insoluble powder |
| --- | --- | --- | --- |
| Example 25 | VA64 (1.0 w/w %) | EDTA2K (10 w/w %) | PMMA powder (0.1 w/w %) |
| Example 26 | VA64 (1.0 w/w %) | EDTA2K (10 w/w %) | Cellulose powder (0.1 w/w %) |
| Example 27 | VA64 (1.0 w/w %) | EDTA2K (10 w/w %) | PMMA powder (5.0 w/w %) |
| Example 28 | VA64 (1.0 w/w %) | EDTA2K (10 w/w %) | Cellulose powder (5.0 w/w %) |
| Example 29 | UMR-30L (1.0 w/w %) | EDTA2K (10 w/w %) | PMMA powder (5.0 w/w %) |
| Example 30 | UMR-30L (1.0 w/w %) | EDTA2K (10 w/w %) | Cellulose powder (5.0 w/w %) |
| Example 31 | UMR-30L (1.0 w/w %) | EDTA2K (10 w/w %) | PMMA powder (0.1 w/w %) |
| Example 32 | UMR-30L (1.0 w/w %) | EDTA2K (10 w/w %) | Cellulose powder (0.1 w/w %) |
| Example 33 | VA64 (1.0 w/w %) | Heparin Li (1000 IU/ml) | PMMA powder (0.1 w/w %) |
| Example 34 | VA64 (1.0 w/w %) | Heparin Li (1000 IU/ml) | Cellulose powder (0.1 w/w %) |
| Example 35 | VA64 (1.0 w/w %) | Heparin Li (1000 IU/ml) | PMMA powder (5.0 w/w %) |
| Example 36 | VA64 (1.0 w/w %) | Heparin Li (1000 IU/ml) | Cellulose powder (5.0 w/w %) |
| Example 37 | UMR-30L (1.0 w/w %) | Heparin Li (1000 IU/ml) | PMMA powder (0.1 w/w %) |
| Example 38 | UMR-30L (1.0 w/w %) | Heparin Li (1000 IU/ml) | Cellulose powder (0.1 w/w %) |
| Example 39 | UMR-30L (1.0 w/w %) | Heparin Li (1000 IU/ml) | PMMA powder (5.0 w/w %) |
| Example 40 | UMR-30L (1.0 w/w %) | Heparin Li (1000 IU/ml) | Cellulose powder (5.0 w/w %) |
| Comparative Example 10 | VA64 (1.0 w/w %) | EDTA2K (10 w/w %) | Not used |
| Comparative Example 11 | UMR-30L (1.0 w/w %) | EDTA2K (10 w/w %) | Not used |
| Comparative Example 12 | VA64 (1.0 w/w %) | Heparin Li (1000 IU/ml) | Not used |
| Comparative Example 13 | UMR-30L (1.0 w/w %) | Heparin Li (1000 IU/ml) | Not used |

Aqueous suspensions of the respective compositions according to Examples 25 to 40 and aqueous solutions of the respective compositions according to Comparative Examples 10 to 13 were prepared and about 30 μl of each suspension or solution was spray-coated on the inside wall of a polyethylene terephthalate) blood sampling tube of 7 ml capacity. The tubes were then allowed to sit in the upright position at 60° C. overnight to dry. Then, the retentivity of each composition on the inside wall of the tube was visually evaluated. The results are shown in Table 9. The results of these Examples and Comparative Examples indicate that the concomitant use of a finely divided insoluble powder results in a marked improvement in the retentivity of the suspension or solution on the inside wall of the tube.

TABLE 9

| Example | 25 | 26 | 27 | 28 | 29 | 30 | 31 | 32 |
| --- | --- | --- | --- | --- | --- | --- | --- | --- |
| Retentivity | Good | Good | Good | Good | Good | Good | Good | Good |
| Example | 33 | 34 | 35 | 36 | 37 | 38 | 39 | 40 |
| Retentivity | Good | Good | Good | Good | Good | Good | Good | Good |

TABLE 9-continued

| Comparative Example | 10 | 11 | 12 | 13 |
|---|---|---|---|---|
| Retentivity | Marked sagging | Marked sagging | Marked sagging | Marked sagging |

Then, a plasma separator (S-Collect, Sekisui Kagaku Kogyo Kabushiki Raisha), 0.9 g/tube, was introduced into all the blood sampling tubes.

Then, 3 ml/tube of fresh rabbit blood was drawn into all the blood sampling tubes, which were then inverted once for gentle blending. The tubes were then allowed to sit at the room temperature of about 23° C. for 30 minutes. Thereafter, each tube was centrifuged at 1300 G for 5 minutes and immediately the deposition status of solid elements of blood on the inside wall above the plasma separator partition was visually evaluated. The results are shown in Table 10. Because of the intentional insufficient blending, the Comparative Examples in which most of the composition was buried in the plasma separator failed to show adequate anticoagulation effects with small amounts of the clot adhering to the tube wall in a ring fashion at the liquid level. In the Examples, however, satisfactory anticoagulation effects were obtained.

TABLE 10

| Example | 25 | 26 | 27 | 28 | 29 | |
|---|---|---|---|---|---|---|
| Retentivity | No adhesion | No adhesion | No adhesion | No adhesion | No adhesion | |
| Example | 30 | 31 | 32 | 33 | 34 | |
| Retentivity | No adhesion | No adhesion | No adhesion | No adhesion | No adhesion | |
| Example | 35 | 36 | 37 | 38 | 39 | 40 |
| Retentivity | No adhesion | No adhesion | No adhesion | No adhesion | No adhesion | No adhesion |
| Comparative Example | 10 | | 11 | | 12 | 13 |
| Retentivity | A small amount of clot adhered in ring form at liquid level | | A small amount of clot adhered in ring form at liquid level | | A small amount of clot adhered in ring form at liquid level | A small amount of clot adhered in ring form at liquid level |

Then, from each blood sampling tube, one-half of the plasma was taken (initial baseline sample) and stored frozen at −20° C. in a 5 ml poly(ethylene terephthalate) tube. The remaining one-half of plasma was stored as it was at 4° C. for 20 hours and, then, stored frozen in a 5 ml poly(ethylene terephthalate) tube (20-hour storage sample) in the same manner.

Forty-eight (48) hours after blood sampling, β-TG was assayed in Examples 25 to 32 and Comparative Examples 10 and 11 and LDH and K were assayed in Examples 33 to 40 and Comparative Examples 12 and 13. The results are shown in Table 11. While β-TG is a substance contained at a high concentration in the platelets and LDH and K+ are substances contained at high concentrations in both the platelets and erythrocytes, these substances are released when the blood cells are stimulated or destroyed. In the Examples wherein a sufficient amount of the composition was retained on the inside wall of the tube, there was no deposition of blood cells on the inside wall so that the measured values after 20 hours of storage were not much different from the initial baseline values. In the Comparative Examples, in which small amounts of the clot were adhering to the inside wall, β-TG showed higher values, both initially and after 20 hours of storage, than in the Examples and LDH and K+ showed upward changes in the course of 20 hours' storage.

TABLE 11

| | β -TG (ng/ml) | |
|---|---|---|
| | Initial sample | Sample after 20 hr of standing |
| Example 25 | 37 | 39 |
| Example 26 | 33 | 31 |
| Example 27 | 35 | 35 |
| Example 28 | 35 | 37 |
| Example 29 | 38 | 35 |
| Example 30 | 35 | 37 |
| Example 31 | 34 | 33 |
| Example 32 | 34 | 35 |
| Comparative Example 10 | 42 | 58 |
| Comparative Example 11 | 39 | 62 |

TABLE 11-continued

| | LDH (IU/l) | | K (mEq/l) | |
|---|---|---|---|---|
| | Initial sample | Sample after 20 hr of standing | Initial sample | Sample after 20 hr of standing |
| Example 33 | 121 | 123 | 3.9 | 3.9 |
| Example 34 | 118 | 120 | 3.9 | 3.9 |
| Example 35 | 115 | 114 | 3.9 | 3.9 |
| Example 36 | 117 | 117 | 3.8 | 3.9 |
| Example 37 | 117 | 116 | 3.9 | 3.9 |
| Example 38 | 124 | 121 | 3.9 | 3.8 |
| Example 39 | 119 | 122 | 3.9 | 3.9 |
| Example 40 | 121 | 124 | 3.9 | 3.8 |
| Comparative Example 12 | 115 | 161 | 3.9 | 5.3 |
| Comparative Example 13 | 117 | 159 | 3.9 | 5.1 |

Examples 41 to 56 and Comparative
Examples 14 to 17

The formulas for the compositions coated on the inside walls of blood sampling tubes are shown in Table 12. In Table 12, SH3749 means the polyether-modified silicone oil nonionic surfactant SH3749 manufactured by Toray-Dow Corning Silicone Co., Pluronic means the polyoxyethylene-polyoxypropylene block copolymer nonionic surfactant-Pluronic P75 manufactured by Asahi Denka, EDTA2K means dipotassium ethylenediaminetetraacetate (Wako Pure Chemical Industries, Ltd., reagent grade), Heparin Li means the corresponding reagent grade manufactured by Sigma Chemical Company, PMMA powder means a poly(methyl methacrylate) powder having a particle diameter of about 50 $\mu$m (MB-50, manufactured by Sekisui Kagaku Kogyo Kabushiki Kaisha), and Cellulose powder means a finely divided cellulose having a particle diameter of about 20 $\mu$m (reagent grade, Aldrich Chemical Company, Inc.).

TABLE 13

| Example | 41 | 42 | 43 | 44 | 45 | 46 | 47 | 48 |
|---|---|---|---|---|---|---|---|---|
| Retentivity | Good | Good | Good | Good | Good | Good | Good | Good |
| Example | 49 | 50 | 51 | 52 | 53 | 54 | 55 | 56 |
| Retentivity | Good | Good | Good | Good | Good | Good | Good | Good |
| Comparative Example | 14 | | 15 | | 16 | | 17 | |
| Retentivity | Marked sagging | | Marked sagging | | Marked sagging | | Marked sagging | |

Then, a plasma separator (S-Collect, Sekisui Kagaku Kogyo Kabushiki Kaisha), 0.9 g/tube, was introduced into all the blood sampling tubes.

TABLE 12

| | Nonionic surfactant | Blood anticoagulant | Finely divided insoluble powder |
|---|---|---|---|
| Example 41 | SH3749 (0.3 w/w %) | EDTA2K (10 w/w %) | PMMA powder (0.1 w/w %) |
| Example 42 | SH3749 (0.3 w/w %) | EDTA2K (10 w/w %) | Cellulose powder (0.1 w/w %) |
| Example 43 | SH3749 (0.3 w/w %) | EDTA2K (10 w/w %) | PMMA powder (5.0 w/w %) |
| Example 44 | SH3749 (0.3 w/w %) | EDTA2K (10 w/w %) | Cellulose powder (5.0 w/w %) |
| Example 45 | Pluronic (0.3 w/w %) | EDTA2K (10 w/w %) | PMMA powder (5.0 w/w %) |
| Example 46 | Pluronic (0.3 w/w %) | EDTA2K (10 w/w %) | Cellulose powder (5.0 w/w %) |
| Example 47 | Pluronic (0.3 w/w %) | EDTA2K (10 w/w %) | PMMA powder (0.1 w/w %) |
| Example 48 | Pluronic (0.3 w/w %) | EDTA2K (10 w/w %) | Cellulose powder (0.1 w/w %) |
| Example 49 | SH3749 (0.3 w/w %) | Heparin Li (1000 IU/ml) | PMMA powder (0.1 w/w %) |
| Example 50 | SH3749 (0.3 w/w %) | Heparin Li (1000 IU/ml) | Cellulose powder (0.1 w/w %) |
| Example 51 | SH3749 (0.3 w/w %) | Heparin Li (1000 IU/ml) | PMMA powder (5.0 w/w %) |
| Example 52 | SH3749 (0.3 w/w %) | Heparin Li (1000 IU/ml) | Cellulose powder (5.0 w/w %) |
| Example 53 | Pluronic (0.3 w/w %) | Heparin Li (1000 IU/ml) | PMMA powder (0.1 w/w %) |
| Example 54 | Pluronic (0.3 w/w %) | Heparin Li (1000 IU/ml) | Cellulose powder (0.1 w/w %) |
| Example 55 | Pluronic (0.3 w/w %) | Heparin Li (1000 IU/ml) | PMMA powder (5.0 w/w %) |
| Example 56 | PIuronic (0.3 w/w %) | Heparin Li (1000 IU/ml) | Cellulose powder (5.0 w/w %) |
| Comparative Example 14 | SB3749 (0.3 w/w %) | EDTA2K (10 w/w %) | Not used |
| Comparative Example 15 | Pluronic (0.3 w/w %) | EDTA2K (10 w/w %) | Not used |
| Comparative Example 16 | SH3749 (0.3 w/w %) | Heparin Li (1000 IU/ml) | Not used |
| Comparative Example 17 | Pluronic (0.3 w/w %) | Heparin Li (1000 IU/ml) | Not used |

Aqueous suspensions of the respective compositions according to Examples 41 to 56 and aqueous solutions of the respective compositions according to Comparative Examples 14 to 17 were prepared and about 30 $\mu$l of each suspension or solution was spray-coated on the inside wall of a poly(ethylene terephthalate) blood sampling tube of 7 ml capacity. The tubes were then allowed to sit in the upright position at 60° C. overnight to dry. Then, the retentivity of each composition on the inside wall of the tube was visually evaluated. The results are shown in Table 13. The results of these Examples and Comparative Examples indicate that the concomitant use of a finely divided insoluble powder results in a marked improvement in the retentivity of the suspension or solution on the inside wall of the tube.

Then, 3 ml/tube of fresh rabbit blood was drawn into all the blood sampling tubes, which were then inverted once for gentle blending. The tubes were then allowed to sit at the room temperature of about 23° C. for 30 minutes. Thereafter, each tube was centrifuged at 1300 G for 5 minutes and immediately the deposition status of cellular elements of blood on the inside wall above the plasma separator partition was visually evaluated. The results are shown in Table 14. Because of the intentional insufficient blending, the Comparative Examples in which most of the composition was buried in the plasma separator failed to show adequate anticoagulation effects with small amounts of the clot adhering to the tube in a ring fashion at the liquid level. In the Examples, however, satisfactory anticoagulation effects were obtained.

TABLE 14

| Example | 41 | 42 | 43 | 44 | 45 | |
|---|---|---|---|---|---|---|
| Retentivity | No adhesion | No adhesion | No adhesion | No adhesion | No adhesion | |
| Example | 46 | 47 | 48 | 49 | 50 | |
| Retentivity | No adhesion | No adhesion | No adhesion | No adhesion | No adhesion | |
| Example | 51 | 52 | 53 | 54 | 55 | 56 |
| Retentivity | No adhesion | No adhesion | No adhesion | No adhesion | No adhesion | No adhesion |
| Comparative Example | 14 | | 15 | | 16 | 17 |
| Retentivity | A small amount of clot adhered in ring form at liquid level | | A small amount of clot adhered in ring form at liquid level | | A small amount of clot adhered in ring form at liquid level | A small amount of clot adhered in ring form at liquid level |

Then, from all the blood sampling tubes, one-half of the plasma was taken (initial baseline samples) and stored frozen at −20° C. in a 5 ml poly(ethylene terephthalate) tube. The remaining one-half of plasma was stored as it was at 4° C. for 20 hours and, then, stored frozen in a 5 ml poly(ethylene terephthalate) tube (20-hour storage samples) in the same manner.

Forty-eight (48) hours after blood sampling, β-TG was assayed in Examples 41 to 48 and comparative Examples 14 and 15 and LDH and K were assayed in Examples 49 to 56 and comparative Examples 16 and 17. The results are shown in Table 15. While β-TG is a substance contained at a high concentration in the platelets and LDH and K+ are substances contained at high concentrations in both the platelets and erythrocytes, these substances are released when the blood cells are stimulated or destroyed. In the Examples wherein a sufficient amount of the composition was retained on the inside wall of the tube, there was no deposition of cellular blood components on the inside wall so that the measured values after 20 hours of storage were not much different from the initial baseline values. In the Comparative Examples, in which small amounts of the clot were adhering to the inside wall, β-TG showed higher values, both initially and after 20 hours' storage, than in the Examples and LDH and K+ showed upward changes in the course of 20 hours' storage.

TABLE 15

| | β-TG (ng/ml) | |
|---|---|---|
| | Initial sample | Sample after 20 hr of standing |
| Example 41 | 41 | 43 |
| Example 42 | 43 | 42 |
| Example 43 | 45 | 44 |
| Example 44 | 41 | 44 |
| Example 45 | 41 | 44 |
| Example 46 | 45 | 41 |
| Example 47 | 43 | 44 |
| Example 48 | 44 | 47 |
| Comparative Example 14 | 58 | 75 |
| Comparative Example 15 | 54 | 69 |

TABLE 15-continued

| | LDH (IU/l) | | K (mEq/l) | |
|---|---|---|---|---|
| | Initial sample | Sample after 20 hr of standing | Initial sample | Sample after 20 hr of standing |
| Example 49 | 176 | 175 | 3.8 | 3.9 |
| Example 50 | 180 | 179 | 3.8 | 3.9 |
| Example 51 | 181 | 175 | 3.8 | 3.9 |
| Example 52 | 181 | 180 | 3.9 | 3.9 |
| Example 53 | 180 | 175 | 3.9 | 3.9 |
| Example 54 | 178 | 175 | 3.9 | 3.9 |
| Example 55 | 180 | 178 | 3.9 | 3.9 |
| Example 56 | 179 | 183 | 3.9 | 3.9 |
| Comparative Example 16 | 183 | 256 | 4.0 | 5.9 |
| Comparative Example 17 | 180 | 248 | 4.0 | 5.8 |

Examples 57 to 72 and Comparative Examples 18 to 25

The formulas for the compositions coated on the inside walls of blood sampling tubes are shown in Tables 16 and 17. In Tables 16 and 17, Modified silicone oil means the carbinol-modified silicone oil SF8427 manufactured by Toray-Dow Corning Silicone Co., Sorbitan monooleate means the corresponding reagent grade manufactured by Wako Pure Chemical Industries, Ltd., PVP means the polyvinylpyrrolidone K-30 manufactured by BASF, PEG means the poly(ethylene glycol) with a number average molecular weight of about 10000 (manufactured by Aldrich Chemical Company, Inc., reagent grade), EDTA2K means dipotassium ethylenediaminetetraacetate (Wako Pure Chemical Industries, Ltd., reagent grade), Heparin Li means the corresponding reagent grade manufactured by Sigma Chemical Company, PMMA powder means a poly(methyl methacrylate)powder having a particle diameter of about 50 μm (MB-50, manufactured by Sekisui Kagaku Kogyo Kabushiki Kaisha), and Cellulose powder means a finely divided cellulose having a particle diameter of about 20 μm (reagent grade, Aldrich Chemical Company, Inc.).

TABLE 16

| | Practically insoluble substance | Water-soluble substance | Blood anticoagulant | Finely divided insoluble powder |
|---|---|---|---|---|
| Example 57 | Modified silicone oil (1.0 w/w %) | PVP (1.0 w/w %) | EDTA2K (10 w/w %) | PMMA powder (0.1 w/w %) |
| Example 58 | Modified silicone oil (1.0 w/w %) | PVP (1.0 w/w %) | EDTA2K (10 w/w %) | Cellulose powder (0.1 w/w %) |
| Example 59 | Modified silicone oil (1.0 w/w %) | PEG (1.0 w/w %) | EDTA2K (10 w/w %) | PMMA powder (5.0 w/w %) |
| Example 60 | Modified silicone oil (1.0 w/w %) | PEG (1.0 w/w %) | EDTA2K (10 w/w %) | Cellulose powder (5.0 w/w %) |
| Example 61 | Sorbitan monooleate (1.0 w/w %) | PVP (1.0 w/w %) | EDTA2K (10 w/w %) | PMMA powder (5.0 w/w %) |
| Example 62 | Sorbitan monooleate (1.0 w/w %) | PVP (1.0 w/w %) | EDTA2K (10 w/w %) | Cellulose powder (5.0 w/w %) |
| Example 63 | Sorbitan monooleate (1.0 w/w %) | PEG (1.0 w/w %) | EDTA2K (10 w/w %) | PMMA powder (0.1 w/w %) |
| Example 64 | Sorbitan monooleate (1.0 w/w %) | PEG (1.0 w/w %) | EDTA2K (10 w/w %) | Cellulose powder (0.1 w/w %) |
| Example 65 | Modified silicone oil (1.0 w/w %) | PVP (1.0 w/w %) | Heparin Li (1000 IU/ml) | PMMA powder (0.1 w/w %) |
| Example 66 | Modified silicone oil (1.0 w/w %) | PVP (1.0 w/w %) | Heparin Li (1000 IU/ml) | Cellulose powder (0.1 w/w %) |
| Example 67 | Modified silicone oil (1.0 w/w %) | PEG (1.0 w/w %) | Heparin Li (1000 IU/ml) | PMMA powder (5.0 w/w %) |
| Example 68 | Modified silicone oil (1.0 w/w %) | PEG (1.0 w/w %) | Heparin Li (1000 IU/ml) | Cellulose powder (5.0 w/w %) |
| Example 69 | Sorbitan monooleate (1.0 w/w %) | PVP (1.0 w/w %) | Heparin Li (1000 IU/ml) | PMMA powder (0.1 w/w %) |
| Example 70 | Sorbitan monooleate (1.0 w/w %) | PVP (1.0 w/w %) | Heparin Li (1000 IU/ml) | Cellulose powder (0.1 w/w %) |
| Example 71 | Sorbitan monooleate (1.0 w/w %) | PEG (1.0 w/w %) | Heparin Li (1000 IU/ml) | PMMA powder (5.0 w/w %) |
| Example 72 | Sorbitan monooleate (1.0 w/w %) | PEG (1.0 w/w %) | Heparin Li (1000 IU/ml) | Cellulose powder (5.0 w/w %) |

TABLE 17

| | Practically insoluble substance | Water-soluble substance | Blood anticoagulant | Finely divided insoluble powder |
|---|---|---|---|---|
| Comparative Example 18 | Modified silicone oil (1.0 w/w %) | PVP (1.0 w/w %) | EDTA2K (10 w/w %) | Not used |
| Comparative Example 19 | Modified silicone oil (1.0 w/w %) | PEG (1.0 w/w %) | EDTA2K (10 w/w %) | Not used |
| Comparative Example 20 | Sorbitan monooleate (1.0 w/w %) | PVP (1.0 w/w %) | EDTA2K (10 w/w %) | Not used |
| Comparative Example 21 | Sorbitan monooleate (1.0 w/w %) | PEG (1.0 w/w %) | EDTA2K (10 w/w %) | Not used |
| Comparative Example 22 | Modified silicone oil (1.0 w/w %) | PVP (1.0 w/w %) | Heparin Li (1000 IU/ml) | Not used |
| Comparative Example 23 | Modified silicone oil (1.0 w/w %) | PEG (1.0 w/w %) | Heparin Li (1000 IU/ml) | Not used |
| Comparative Example 24 | Sorbitan monooleate (1.0 w/w %) | PVP (1.0 w/w %) | Heparin Li (1000 IU/ml) | Not used |
| Comparative Example 25 | Sorbitan monooleate (1.0 w/w %) | PEG (1.0 w/w %) | Heparin Li (1000 IU/ml) | Not used |

Aqueous suspensions of the respective compositions according to Examples 57 to 72 and aqueous solutions of the respective compositions according to Comparative Examples 14 to 17 were prepared and about 30 µl of each suspension or solution was spray-coated on the inside wall of a poly(ethylene terephthalate) blood sampling tube of 7 ml capacity. The tubes were then allowed to sit in the upright position at 60° C. overnight to dry. Then, the retentivity of each composition on the inside wall of the tube was visually evaluated. The results are shown in Table 17. The results of these Examples and Comparative Examples indicate that the concomitant use of a finely divided insoluble substance results in a marked improvement in the retentivity of the suspension or solution on the inside wall of the tube.

TABLE 18

| Example | 57 | 58 | 59 | 60 | 61 | 62 | 63 | 64 |
|---|---|---|---|---|---|---|---|---|
| Retentivity | Good | Good | Good | Good | Good | Good | Good | Good |
| Example | 65 | 66 | 67 | 68 | 69 | 70 | 71 | 72 |
| Retentivity | Good | Good | Good | Good | Good | Good | Good | Good |
| Comparative Example | 18 | 19 | 20 | 21 | | | | |
| Retentivity | Marked sagging | Marked sagging | Marked sagging | Marked sagging | | | | |

TABLE 18-continued

| Comparative Example | 22 | 23 | 24 | 25 |
|---|---|---|---|---|
| Retentivity | Marked sagging | Marked sagging | Marked sagging | Marked sagging |

Then, a plasma separator (S-Collect, Sekisui Kagaku Kogyo Kabushiki Kaisha), 0.9 g/tube, was introduced into all the blood sampling tube.

Then, 3 ml/tube of fresh rabbit blood was drawn into all the blood sampling tubes, which were then inverted once for gentle blending. The tubes were then allowed to sit at the room temperature of about 23° C. for 30 minutes. Thereafter, each tube was centrifuged at 1300 G for 5 minutes and immediately the deposition status of cellular elements of blood on the inside wall above the plasma separator partition was visually evaluated. The results are shown in Table 18. Because of intentional insufficient blending, the Comparative Examples in which most of the composition was buried in the plasma separator failed to show adequate anticoagulation effects with small amounts of the clot adhering to the tube in a ring fashion at the liquid level. In the Examples, however, satisfactory anticoagulation effects were obtained.

TABLE 19

| Example | 57 | 58 | 59 | 60 | 61 | |
|---|---|---|---|---|---|---|
| Retentivity | No adhesion | No adhesion | No adhesion | No adhesion | No adhesion | |
| Example | 62 | 63 | 64 | 65 | 66 | |
| Retentivity | No adhesion | No adhesion | No adhesion | No adhesion | No adhesion | |
| Example | 67 | 68 | 69 | 70 | 71 | 72 |
| Retentivity | No adhesion | No adhesion | No adhesion | No adhesion | No adhesion | No adhesion |
| Comparative Example | 18 | 19 | 20 | 21 | | |
| Retentivity | A small amount of clot adhered in ring form at liquid level | A small amount of clot adhered in ring form at liquid level | A small amount of clot adhered in ring form at liquid level | A small amount of clot adhered in ring form at liquid level | | |
| Comparative Example | 22 | 23 | 24 | 25 | | |
| Retentivity | A small amount of clot adhered in ring form at liquid level | A small amount of clot adhered in ring form at liquid level | A small amount of clot adhered in ring form at liquid level | A small amount of clot adhered in ring form at liquid level | | |

Then, from all the blood sampling tubes, one-half of the plasma was taken (initial baseline samples) and stored frozen at −20° C. in a 5 ml poly(ethylene terephthalate) tube. The remaining one-half of plasma was stored as it was at 4° C. for 20 hours and, then, stored frozen in a 5 ml poly (ethylene terephthalate) tube (20-hour storage samples) in the same manner.

Forty-eight (48) hours after blood sampling, β-TG was assayed in Examples 56 to 63 and Comparative Examples 18 to 21 and LDH and K were assayed in Examples 64 to 72 and Comparative Examples 22 to 25. The results are shown in Tables 19 and 20. While β-TG is a substance contained at a high level in the platelets and LDH and K+ are substances occurring at high concentrations in both the platelets and erythrocytes, these substances are released when the blood cells are stimulated or destroyed. In the Examples wherein a sufficient amount of the composition was retained on the inside wall of the tube, there was no deposition of blood cells on the inside wall so that the measured values after 20 hours of storage were not much different from the initial baseline values. In the Comparative Examples, in which small amounts of the clot were adhering to the inside wall, β-TG showed higher values, both initially and after 20 hours of storage, than in the Examples and LDH and K+ showed upward changes in the course of 20 hours' storage.

TABLE 20

| | β-TG (ng/ml) | |
|---|---|---|
| | Initial sample | Sample after 20 hr of standing |
| Example 57 | 25 | 27 |
| Example 58 | 25 | 26 |
| Example 59 | 23 | 26 |
| Example 60 | 27 | 25 |
| Example 61 | 26 | 23 |
| Example 62 | 23 | 25 |
| Example 63 | 23 | 25 |
| Example 64 | 25 | 27 |
| Comparative Example 18 | 33 | 49 |
| Comparative Example 19 | 34 | 51 |
| Comparative Example 20 | 32 | 53 |
| Comparative Example 21 | 27 | 39 |

TABLE 21

| | LDH (IU/l) | | K (mEq/l) | |
|---|---|---|---|---|
| | Initial sample | Sample after 20 hr of standing | Initial sample | Sample after 20 hr of standing |
| Example 65 | 130 | 135 | 3.8 | 3.9 |
| Example 66 | 125 | 130 | 3.8 | 3.8 |
| Example 67 | 127 | 130 | 3.8 | 3.8 |
| Example 68 | 132 | 128 | 3.7 | 3.9 |
| Example 69 | 122 | 126 | 3.8 | 3.8 |
| Example 70 | 136 | 133 | 3.8 | 3.7 |
| Example 71 | 131 | 135 | 3.8 | 3.8 |
| Example 72 | 135 | 132 | 3.7 | 3.9 |
| Comparative Example 22 | 129 | 156 | 3.8 | 4.8 |
| Comparative Example 23 | 135 | 164 | 3.7 | 5.3 |
| Comparative Example 24 | 131 | 158 | 3.7 | 5.1 |
| Comparative Example 25 | 133 | 167 | 3.8 | 5.1 |

INDUSTRIAL APPLICABILITY

With the blood test ware of the present invention, blood coagulation factors are rapidly activated to shorten the clotting time in a significant degree and, at the same time, the deposition of the resulting clot on the inside wall of the ware is precluded, with the result that separation of the serum from the clot is facilitated and contamination of the serum with components of the clot is prevented. The serum yield is also remarkably increased.

What is claimed is:

1. A composition for preventing deposition of blood components to the inner surface of a blood test ware or to the surface of a matrix, wherein said composition comprises a blood anticoagulant and a random copolymer comprising 10 to 70 mol % of vinylprrolidone and correspondingly 90 to 30 mol % of vinyl acetate, said matrix comprising a support and said composition being caused to be present on the surface of the inner wall of the blood test ware or of the support to prevent deposition of blood components on the surface thereof, and wherein said inner wall or support of said matrix comprises a material selected from the group consisting of thermoplastic resin, thermosetting resin, modified natural resin and glass.

2. The composition according to claim 1, wherein said blood anticoagulant is at least one member selected from the group consisting of a salt of ethylenediaminetetraacetic acid, a salt of citric acid, a heparin salt and a salt of oxalic acid.

3. The composition according to claim 1, which further comprises an adsorbent inorganic material.

4. The composition according to claim 3, wherein said adsorbent inorganic material is at least one member selected from the group consisting of glass, kaoline, bentonite, silica and cerite.

5. The composition according to claim 3, wherein said adsorbent inorganic material has a linseed oil absorption value of 20 to 40 ml/100 g and a BET specific surface area value of 5,000 to 30,000 $cm^2/g$.

6. The composition according to claim 3, wherein said adsorbent inorganic material has a resistivity value of not larger than $1 \times 10^{10}$ Ω.cm.

7. The composition according to claim 1, which further comprises an organic blood-coagulation-accelerating substance.

8. The composition according to claim 7, wherein said organic blood-coagulation-accelerating substance is ellagic acid.

9. The composition according to claim 1, which farther comprises an antiglycolytic agent.

10. The composition according to claim 9, wherein said antiglycolytic agent is a fluoride or mannose or both.

11. The composition according to claim 1, wherein said blood test ware or matrix are intended for hematological, serum biochemical or immunoserological examinations of a blood sample.

12. A blood test ware comprising a blood test vessel having an inner surface and a composition disposed on the inner surface, wherein said composition comprises a blood anticoagulant and a random copolymer comprising 10 to 70 mol % of vinylprrolidone and correspondingly 90 to 30 mol % of vinyl acetate.

13. The blood test ware according to claim 12, wherein said blood anticoagulant is at least one member selected from the group consisting of a salt of ethylenediaminetetraacetic acid, a salt of citric acid, a heparin salt and a salt of oxalic acid.

14. The blood test ware according to claim 12, wherein the amount of the composition present on the inner surface is $1 \times 10^{-10}$ to $1 \times^{-2}$ $g/cm^2$.

15. The blood test ware according to claim 12, wherein the vessel comprises a material selected from the group consisting of thermoplastic resin, thermosetting resin, modified natural resin and glass.

16. The blood test ware according to claim 12, which is further comprises a serum/plasma separator.

17. The blood test ware according to claim 12, which is intended for hematological, serum biochemical or immunoserological examinations of a blood sample.

18. A blood test vessel comprising a blood component deposition-preventing matrix therein, wherein the matrix comprises a support containing a composition disposed on a surface thereof, and said composition comprises blood anticoagulant and random copolymer comprising 10 to 70 mol % of vinylpyrrolidone and correspondingly 90 to 30 mol % of vinyl acetate.

19. The blood test vessel according to claim 18, wherein said blood anticoagulant is at least one member selected from the group consisting of a salt of ethylenediaminetetraacetic acid, a salt of citric acid, a heparin salt and a salt of oxalic acid.

20. The blood test vessel according to claim 18, wherein the amount of the composition present on the surface of the support is $1 \times 10^{-10}$ to $1 \times 10^{-2}$ $g/cm^2$.

21. The blood test according to claim 18, wherein said support comprises thermoplastic resin, thermosetting resin and modified natural resin.

22. A method for preventing deposition of blood components to the inner surface of a blood test ware or to the surface of a matrix, said matrix comprising a support, which comprises causing a composition to be present on the surface of the inner wall of the blood test ware or of the support, wherein said composition comprises a blood anticoagulant and a random copolymer comprising 10 to 70 mol % of vinylprrolidone and correspondingly 90 to 30 mol % of vinyl acetate, and said inner wall or support of said matrix comprises a material selected from the group consisting of thermoplastic resin, thermosetting resin, modified natural resin and glass.

23. The method according to claim 22, wherein said blood anticoagulant is at least one member selected from the group consisting of a salt of ethylenediaminetetraacetic acid, a salt of citric acid, a heparin salt and a salt of oxalic acid.

24. The method according to claim 22, which comprises kneading said random copolymer into a plastic batch and molding the kneaded mixture to prepare said blood test ware or said support, to cause said random copolymer to be present on the surface of the inner wall of the blood test ware or of the support, and applying said blood anticoagulant to the inner wall of said blood test ware or to the surface of said support by spray coating or dip coating, in order to cause said composition to be present on the surface of the inner wall of the blood test ware or of the support.

25. The method according to claim 22, which comprises, dissolving said random copolymer in pure water or alcohol to obtain a solution, applying the solution to the inner wall of said blood test ware or to the surface of said support by spray coating or dip coating, and drying the coat, to cause said composition to be present on the surface of the inner wall of the blood test ware or of the support.

26. The method according to claim 22, which comprises dissolving or suspending said composition in a medium to obtain a solution or a suspension, applying the solution or the suspension to the inner wall of said blood test were or to the surface of said support by spray coating or dip coating, and drying the coat, in order to cause said composition to be present on the surface of the inner wall of the blood test ware or of the support.

* * * * *